United States Patent
Axelrod et al.

(10) Patent No.: US 10,555,814 B2
(45) Date of Patent: Feb. 11, 2020

(54) ULTRASOUND PROBE FOR CARDIAC TREATMENT

(71) Applicant: Edwards Lifesciences Corporation, Irvine, CA (US)

(72) Inventors: Noa Axelrod, Herzeliya (IL); Oren Wintner, Jerusalem (IL); Eran Goldberg, Nesher (IL); Dikla Kersh, Karkur (IL); Danny Garnahi, Hadera (IL); Dan Rottenberg, Haifa (IL); Boaz Manash, Givat Ada (IL)

(73) Assignee: Edwards Lifesciences Corporation, Irvine, CA (US)

( * ) Notice: Subject to any disclaimer, the term of this patent is extended or adjusted under 35 U.S.C. 154(b) by 543 days.

(21) Appl. No.: 15/353,666

(22) Filed: Nov. 16, 2016

(65) Prior Publication Data

US 2017/0135818 A1    May 18, 2017

Related U.S. Application Data

(60) Provisional application No. 62/256,524, filed on Nov. 17, 2015, provisional application No. 62/256,527, filed on Nov. 17, 2015.

(51) Int. Cl.
*A61F 2/24*      (2006.01)
*A61B 8/12*      (2006.01)
*A61B 8/00*      (2006.01)

(52) U.S. Cl.
CPC .............. *A61F 2/2445* (2013.01); *A61B 8/12* (2013.01); *A61B 8/42* (2013.01); *A61F 2/2466* (2013.01); *A61F 2/2487* (2013.01)

(58) Field of Classification Search
CPC .... A61F 2/2445; A61F 2/2466; A61F 2/2478; A61F 2/2487
See application file for complete search history.

(56) References Cited

U.S. PATENT DOCUMENTS

| 1,527,291 A | 2/1925 | Zorraquin |
| 2,623,521 A | 12/1952 | Shaw |

(Continued)

FOREIGN PATENT DOCUMENTS

| WO | 2005/102181 A1 | 11/2005 |
| WO | WO/2012/099418 | 7/2012 |
| WO | 2014/134624 A1 | 9/2014 |

OTHER PUBLICATIONS

Herlambang, et al., Realtime Integral Videography Using Intra-Operative 3-D Ultrasound for Minimally Invasive Heart Surgery.

(Continued)

*Primary Examiner* — Carrie R Dorna
(74) *Attorney, Agent, or Firm* — Snell & Wilmer L.L.P.

(57) ABSTRACT

Ultrasound probe systems and methods for using an ultrasound probe to assist during treatment of conditions of the human heart are provided. The method may comprise loading a medical instrument into a guide fastened to the ultrasound probe. The ultrasound probe may be inserted into a patient by way of an incision. The distal end of the ultrasound probe may be navigated to a location adjacent to an exterior surface of the heart. A treatment site may be identified on the exterior surface of the heart based on images obtained from an ultrasound transducer disposed within a distal end of the ultrasound probe. The medical instrument may be advanced within the guide to the treatment site and the medical instrument used for treatment. After treatment, the medical instrument may be withdrawn from the treatment site.

20 Claims, 10 Drawing Sheets

(56) References Cited

U.S. PATENT DOCUMENTS

| | | | |
|---|---|---|---|
| 4,742,829 A | 5/1988 | Law et al. | |
| 5,098,388 A | 3/1992 | Kulkashi et al. | |
| 5,139,485 A | 8/1992 | Smith et al. | |
| 5,226,890 A | 7/1993 | Ianniruberto et al. | |
| 5,258,003 A | 11/1993 | Ciaglia et al. | |
| 5,292,310 A | 3/1994 | Yoon | |
| 5,478,329 A | 12/1995 | Ternamian | |
| 5,591,191 A | 1/1997 | Kieturakis | |
| 5,601,537 A | 2/1997 | Frassica | |
| 5,669,883 A | 9/1997 | Scarfone et al. | |
| 5,671,747 A | 9/1997 | Connor | |
| 5,676,682 A | 10/1997 | Yoon | |
| 5,755,697 A | 5/1998 | Jones et al. | |
| 5,810,776 A | 9/1998 | Bacich et al. | |
| 5,961,440 A | 10/1999 | Schweich, Jr. et al. | |
| 6,007,481 A | 12/1999 | Riek et al. | |
| 6,050,936 A | 4/2000 | Schweich, Jr. et al. | |
| 6,156,006 A | 12/2000 | Brosens et al. | |
| 6,210,336 B1 | 4/2001 | Fredriksen | |
| 6,293,952 B1 | 9/2001 | Brosens et al. | |
| 6,616,684 B1 | 9/2003 | Vidlund et al. | |
| 6,969,354 B1 | 11/2005 | Marian | |
| 7,056,294 B2 | 6/2006 | Khairkhahan et al. | |
| 7,241,267 B2 | 7/2007 | Furia | |
| 7,766,812 B2 | 8/2010 | Schroeder et al. | |
| 8,163,013 B2 | 4/2012 | Machold et al. | |
| 8,425,402 B2 | 4/2013 | Annest et al. | |
| 8,444,566 B2 | 5/2013 | Agmon | |
| 8,500,628 B2 | 8/2013 | Frassica et al. | |
| 8,777,841 B2 | 7/2014 | Frassica et al. | |
| 9,011,531 B2 | 4/2015 | Rourke et al. | |
| 2004/0049211 A1 | 3/2004 | Tremulis et al. | |
| 2005/0075723 A1 | 4/2005 | Schroeder et al. | |
| 2005/0107810 A1* | 5/2005 | Morales | A61B 17/00234 606/143 |
| 2005/0222488 A1 | 10/2005 | Chang et al. | |
| 2006/0052821 A1 | 3/2006 | Abbott et al. | |
| 2006/0122633 A1 | 6/2006 | To et al. | |
| 2006/0259074 A1 | 11/2006 | Kelleher et al. | |
| 2007/0066863 A1 | 3/2007 | Rafiee et al. | |
| 2007/0083168 A1 | 4/2007 | Whiting et al. | |
| 2007/0203391 A1 | 8/2007 | Bloom et al. | |
| 2007/0265658 A1 | 11/2007 | Nelson et al. | |
| 2008/0009888 A1 | 1/2008 | Ewers et al. | |
| 2008/0249467 A1 | 10/2008 | Burnett et al. | |
| 2008/0294251 A1 | 11/2008 | Annest et al. | |
| 2009/0088678 A1 | 4/2009 | Noda et al. | |
| 2009/0093726 A1 | 4/2009 | Takayama et al. | |
| 2009/0118612 A1 | 5/2009 | Grunwald et al. | |
| 2010/0010538 A1 | 1/2010 | Juravic et al. | |
| 2010/0016655 A1 | 1/2010 | Annest et al. | |
| 2010/0160788 A1 | 6/2010 | Davies et al. | |
| 2010/0274081 A1 | 10/2010 | Okoniewski | |
| 2011/0178537 A1 | 7/2011 | Whitman | |
| 2012/0136435 A1 | 5/2012 | Brunnett et al. | |
| 2013/0030522 A1 | 1/2013 | Rowe et al. | |
| 2013/0165735 A1 | 6/2013 | Khairkhahan et al. | |
| 2013/0245450 A1 | 9/2013 | Prins et al. | |
| 2013/0296902 A1 | 11/2013 | Vonderwalde et al. | |
| 2013/0310752 A1 | 11/2013 | Kawaura | |
| 2014/0094647 A1 | 4/2014 | Schweich, Jr. et al. | |
| 2015/0018876 A1 | 1/2015 | Ewers et al. | |
| 2015/0045879 A1 | 2/2015 | Longoria et al. | |
| 2015/0105611 A1 | 4/2015 | Schweich, Jr. et al. | |

OTHER PUBLICATIONS

Flato et al., Ultrasound-Guided Venous Cannulation in a Critical Care Unit, Rev. bras. ter. intensiva vol. 21 No. 2 São Paulo Apr./Jun. 2009, pp. 1-11.

Int'. Search Report for PCT/US2016/062581, dated Mar. 3, 2017.

Int'l. Search Report for PCT/US2016/062556, dated Feb. 27, 2017.

* cited by examiner

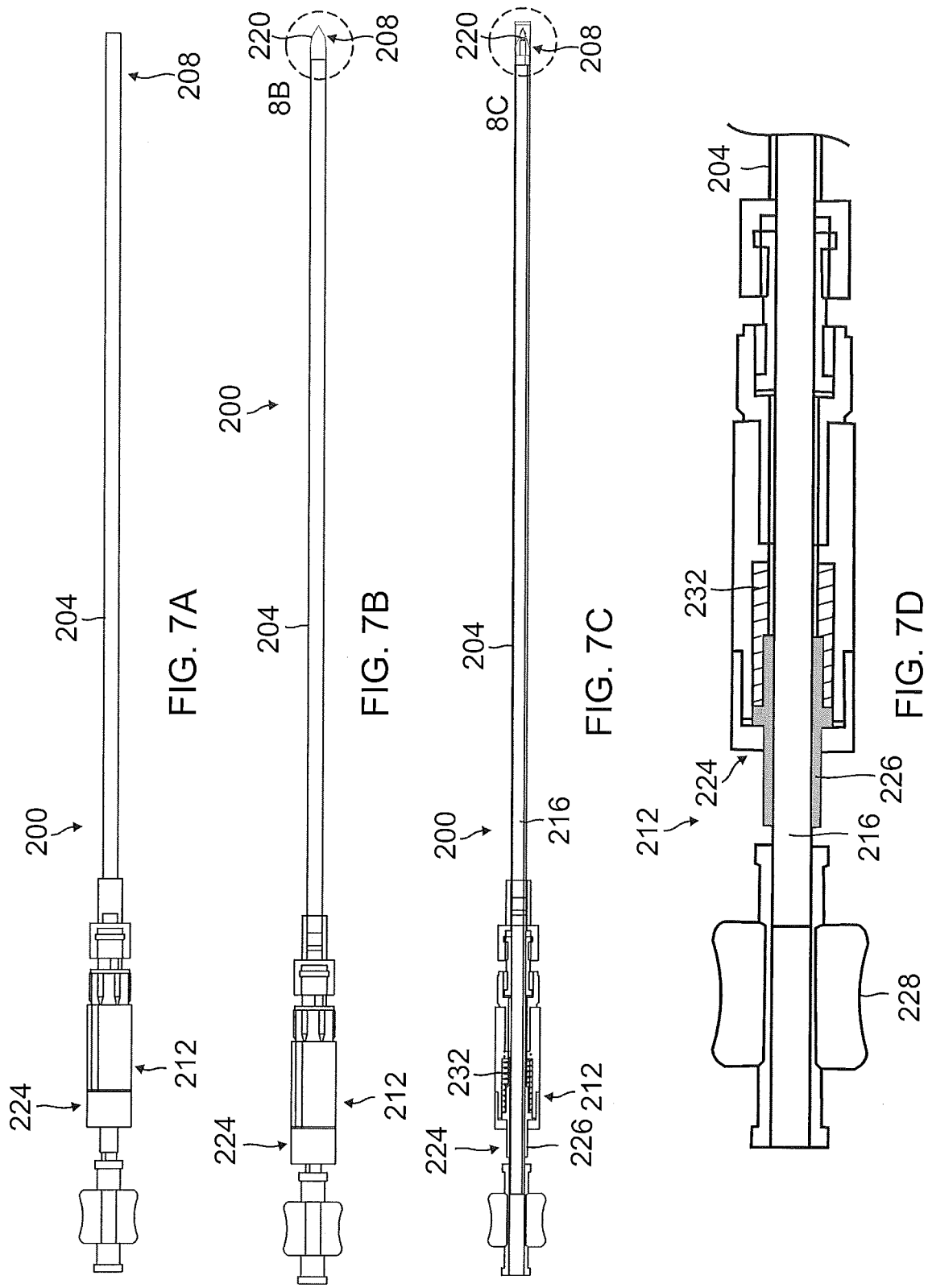

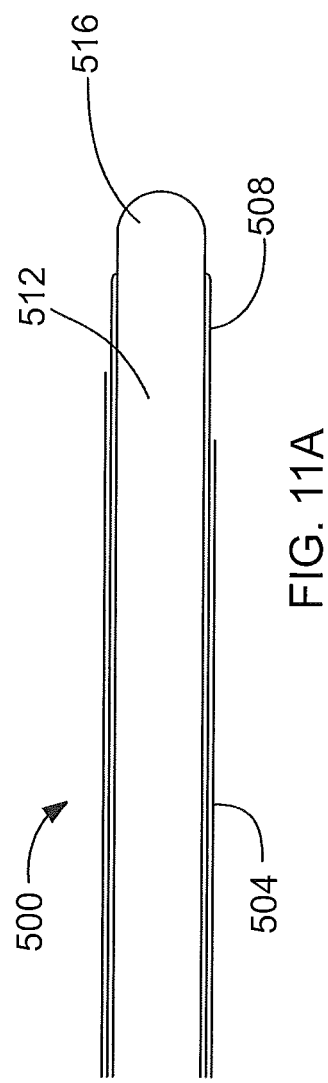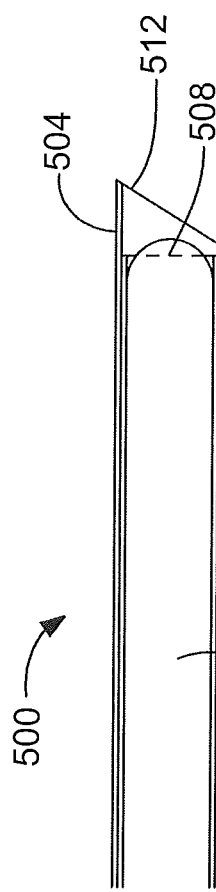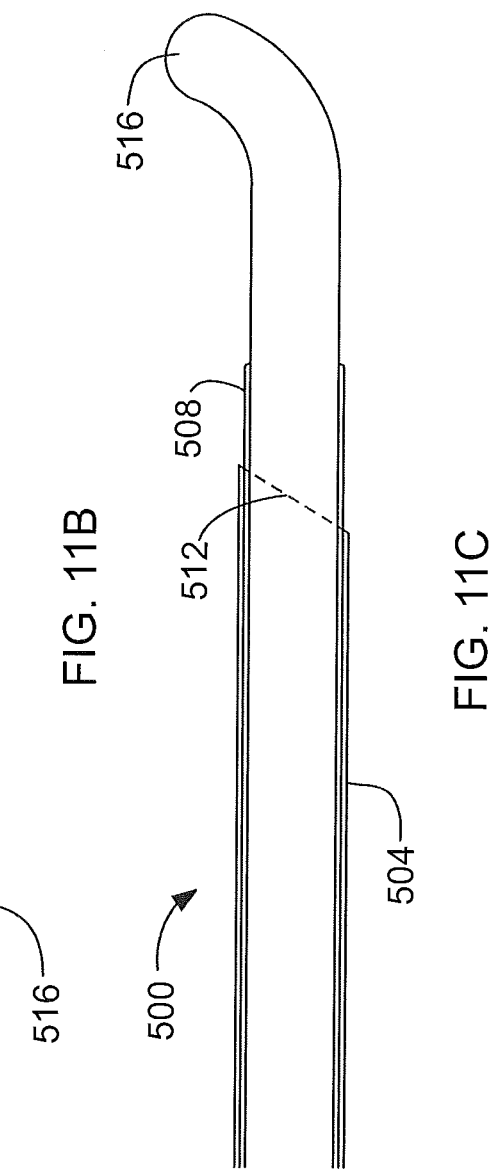

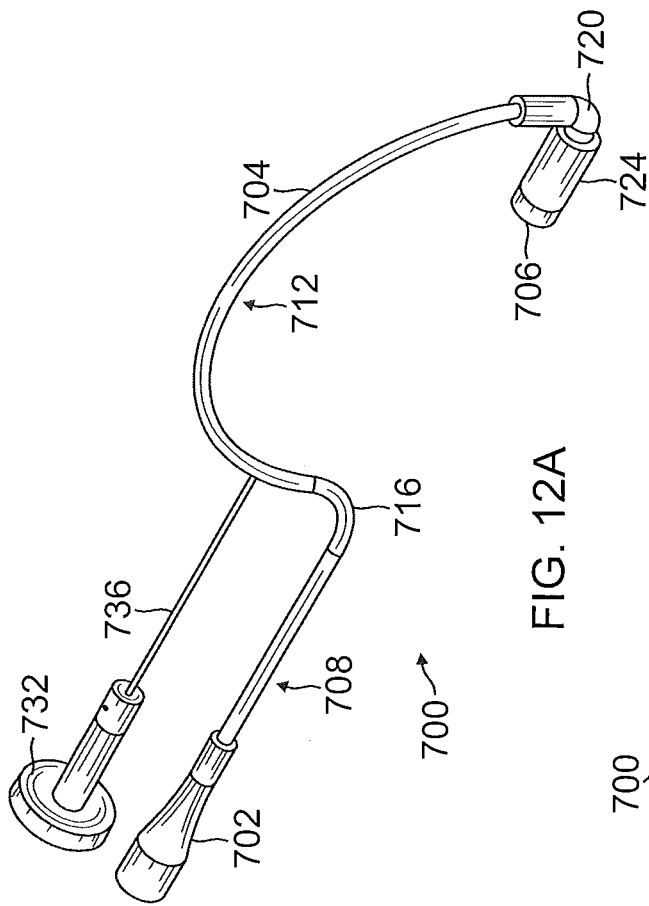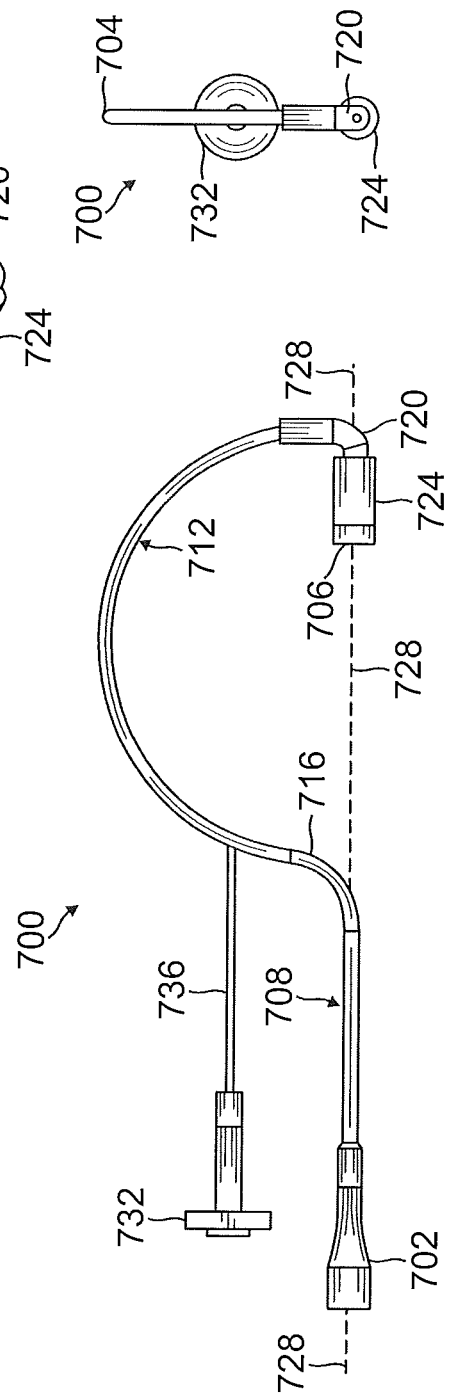

ULTRASOUND PROBE FOR CARDIAC TREATMENT

PRIORITY

This application claims the benefit of and priority to the U.S. Provisional Application, entitled "Ultrasound Probe for Cardiac Treatment," filed on Nov. 17, 2015 having application Ser. No. 62/256,524 and the U.S. Provisional Application, entitled "Systems And Devices For Setting An Anchor," filed on Nov. 17, 2015 having application Ser. No. 62/256,527, both of which applications are incorporated by reference herein in their entirety.

BACKGROUND

Heart failure can occur when the left ventricle of the heart becomes enlarged and dilated as a result of one or more of various etiologies. Initial causes of heart failure can include chronic hypertension, myocardial infarction, mitral valve incompetency, and other dilated cardiomyopathies. With each of these conditions, the heart is forced to overexert itself in order to provide a cardiac output demanded by the body during various demand states. The result can be an enlarged left ventricle.

A dilated or enlarged heart, and particularly a dilated or enlarged left ventricle, can significantly increase tension and stress in heart walls both during diastolic filling and systolic contraction, which contributes to further dilatation or enlargement of chambers of the heart. Prior treatments for heart failure include pharmacological treatments, assist devices such as pumps, and surgical treatments such as heart transplant, dynamic cardiomyoplasty, and Batista partial left ventriculectomy. These prior treatments are described briefly in U.S. Pat. No. 5,961,440, entitled "Heart Wall Tension Reduction Apparatus and Method," issued on Oct. 5, 1999, the entirety of which is incorporated by reference herein.

A more recent concept for treating heart failure applies one or more splints onto the heart, to reduce myocardial muscular stresses encountered during pumping. Examples of such approaches are disclosed in U.S. Pat. No. 7,766,812, entitled "Methods and devices for improving mitral valve function," issued on Aug. 3, 2010, the entirety of which is incorporated herein by reference. One example includes one or more transventricular splints placed across the left ventricle. Each splint may include a tension member extending across the ventricle with anchors disposed on opposite ends of the tension member and placed on the external surface of the heart.

Interventional cardiac procedures in humans generally require a specific access point, and the access point can be limited due to anatomic constraints. A needle or other instrument may need to be inserted through the access point, advanced to the heart without unnecessarily injuring nearby tissues and structures along the way, and then inserted into the heart. In treating mitral valve incompetency, mitral valve regurgitation, and other similar conditions, the needle or other instrument may be advanced across the right ventricle of the heart, passed through the septal wall or septum between the right ventricle and the left ventricle, extended across the left ventricle, and then passed through the posterior wall of the left ventricle. It may be beneficial to perform mitral valve treatments under live echocardiography imaging, so as to enable the surgeon to correctly orient the needle or other instrument during puncturing of the heart and/or other steps in the procedure/treatment. However, it is important not to cause undue trauma and, among other things, ensure that the access point into the patient, entry point into the heart, and any puncture points or incisions should be as small in size as possible so as to reduce trauma to the patient and reduce the time required for recovery. Current epicardial echocardiography probes are not well configured for mitral valve treatments through small access points (e.g., punctures, incisions, holes, etc.). Among other things, there is insufficient room in the access points for insertion of epicardial echocardiography probes, thus limiting visibility during treatment (e.g., during puncturing the heart wall and/or septum). Further, epicardial echocardiography probes are not well suited for being inserted into a small access points or entry points associated with various treatments of the heart (e.g., they are not well suited for treatment of mitral valve incompetencies, mitral valve regurgitation, and other similar conditions), and are not well suited for precise imaging during advancing a needle or other instrument across the right ventricle of the heart, through a small opening/puncture in the septal wall or septum, across the left ventricle, and then passed through the posterior wall of the left ventricle. Also, the probes may provide too narrow of a viewing range. Thus, it would be desirable to have better treatment methods using better configured imaging equipment that provide greater access and visibility to the surgeon during medical treatment, thereby imparting greater benefit to the patient.

The methods, systems, devices, apparatuses, instruments, etc. described herein may be used for medical treatment, for treatment of conditions of the human heart, and for improving heart valve function.

SUMMARY

Systems, assemblies, apparatuses, instruments, and related methods are provided for medical treatment, including using an ultrasound probe (e.g., a trans-vaginal ultrasound probe or an ultrasound probe designed for use in treatment of mitral valve incompetency, mitral valve regurgitation, and other similar conditions) to assist during treatment of conditions of the human heart. The ultrasound probe should be ideally as small as possible, but still provide clear images that may be used for the desired treatment/procedure. The ultrasound probe may be shaped for easy insertion into an access point to the body and into an entry point into the heart and allow for imaging during penetration of the septum between the right ventricle and the left ventricle and penetration of or forming a hole in a posterior wall of the left ventricle. The ultrasound probe may be designed to give a wide angle of view. The ultrasound probe may comprise an elongate shaft extending from a proximal handle to a distal end. The ultrasound probe may include a guide (e.g., an apparatus, jig, attachment mechanism, mount, etc. for attaching and guiding of a medical instrument) attached to the ultrasound probe to form an ultrasound probe system or assembly. The guide may be configured to facilitate easy and secure attachment of one or more medical instruments (e.g., a needle, needle catheter, trocar, etc.) to the ultrasound probe, and may be used to guide the attached medical instruments during treatment. The guide may allow for releasable attachment and may interchangeably attach to multiple different instruments/devices (e.g., for different patients or for different steps in a treatment).

A method may comprise loading a medical instrument into the guide (e.g., attaching the instrument to the guide) of the ultrasound probe. The ultrasound probe (e.g., the trans-vaginal ultrasound probe or ultrasound probe configured for treating mitral valve regurgitation) may be inserted into a patient by way of an access point (e.g., an incision or opening). The probe may also be inserted between ribs, if necessary. The distal end of the ultrasound probe may be navigated to a location adjacent to an exterior surface of the heart and/or pericardium. An ultrasound transducer within the distal end facilitates viewing tissues and structures during navigation of the distal end so as to avoid injury to the patient. A treatment site may be identified on the exterior surface of the heart and/or pericardium based on images (e.g., a live/real-time image) of the heart and/or surrounding tissues obtained using the ultrasound transducer. The medical instrument is advanced within the guide to the treatment site, and the condition of the heart is then treated. Treating the condition of the heart may comprise puncturing, making an incision, making a hole in a wall of the heart to gain access. Treating the condition of the heart may also comprise fixating a mitral valve splint to the heart by way of at least one of a superior anchor and an inferior anchor so as to treat mitral valve incompetency and/or regurgitation. After treatment, the medical instrument may be withdrawn from the treatment site.

In an exemplary embodiment, a method for using an ultrasound probe (e.g., a trans-vaginal ultrasound probe or an ultrasound probe designed for use in treatment of mitral valve incompetency, mitral valve regurgitation, and other similar conditions) for treatment of conditions of the human heart may comprise loading a medical instrument (e.g., needle, trocar, needle catheter, catheter, introducer, introducer assembly, etc.) into a guide of the ultrasound probe (e.g., attaching the medical instrument to the guide), the guide being fastened to an ultrasound probe comprising an elongate shaft extending from a proximal handle to a distal end; and inserting the ultrasound probe into a patient by way of an incision. The method may also comprise navigating the distal end of the ultrasound probe to a location adjacent to an exterior surface of the heart and/or pericardium; identifying a treatment site on an exterior surface of the heart and/or pericardium by way of an ultrasound transducer disposed within the distal end of the ultrasound probe; advancing the medical instrument to the treatment site using the guide; treating the condition of the heart, at least in part, by using the medical instrument; and withdrawing the medical instrument away from the treatment site.

In one exemplary embodiment, the method may further comprise fastening the guide to the ultrasound probe by way of a proximal coupling and a distal coupling. This can be done in a variety of ways and configurations, e.g., in one embodiment, the guide is parallel to the elongate shaft, but other angles relative to the shaft and other arrangements of the guide are possible. If the guide is angled relative to the shaft and/or distal end in a fixed angle and the fixed angle is known, then a user may accurately predict the path of the medical instrument (e.g., needle and/or delivery system). In one embodiment, the angle of the guide may be adjustable and lockable into a variety of angles. The distal end of the medical instrument may be positioned adjacent to the distal end of the ultrasound probe. In one exemplary embodiment, the step of inserting the ultrasound probe into the patient may comprise advancing the distal end of the ultrasound probe and the distal end of the medical instrument together within the patient. In one exemplary embodiment, the step of navigating the distal end of the ultrasound probe to a location may comprise viewing tissues and structures within the patient by way of the ultrasound transducer, e.g., by way of an ultrasound image(s) (e.g., a live/real-time image) obtained by an ultrasound transducer, such that injury to the tissues and structures due to advancing the distal end of the ultrasound probe and the distal end of the medical instrument may be avoided and/or minimized. In one exemplary embodiment, the ultrasound transducer may be configured to provide a view of the tissues and structures directly in front of the distal end of the ultrasound probe and/or to the sides of the ultrasound probe.

In one exemplary embodiment, the step of identifying a treatment site may comprise using the ultrasound transducer to observe structures/physical characteristics of the exterior surface and/or within the heart in search of the treatment site. In one exemplary embodiment, the step of treating the condition of the heart may comprise fixating a mitral valve splint in the heart by way of at least one of a superior anchor and an inferior anchor so as to treat mitral valve incompetency. Access to the heart may be done through the treatment site. In one exemplary embodiment, the at least one or both of the superior anchor and the inferior anchor may comprise a self-expandable anchor suitable for deployment during treatment and may be configured to contact the exterior surface of the heart and/or pericardium. Treating the condition of the heart may include using the medical instrument to facilitate one or more aspects of fixating the mitral valve splint, e.g., puncturing and/or creating a hole in the septum or posterior wall of the left ventricle, delivering one of the anchors, etc.

In one exemplary embodiment, the medical instrument may comprise a trocar catheter, and the step of identifying the treatment site may comprises observing structures/physical characteristics on the exterior surface and/or within the heart to identify a puncture site at which the trocar catheter may be used to puncture the exterior surface and heart wall. In one exemplary embodiment, the step of treating the condition may comprise using an actuator to deploy a trocar distal tip so as to puncture the heart and/or pericardium at the puncture site. The method may further comprise allowing a plunger mechanism to retract the trocar distal tip into an interior lumen of the medical instrument.

In one exemplary embodiment, the medical instrument may comprise a flexible and/or curved needle, and the step of identifying the treatment site may comprise observing structures/physical characteristics on the exterior surface and/or within the heart to identify a first puncture site at which the flexible and/or curved needle may be used to puncture the exterior surface and heart wall. In one exemplary embodiment, the step of treating the condition may comprise using the flexible and/or curved needle to puncture the heart and/or pericardium at the first puncture site. The method may also comprise extending or advancing the flexible and/or curved needle across the right ventricle of the heart to the septal wall or septum. The method may also comprise using the ultrasound transducer to identify a second puncture site, e.g., on the septal wall or septum between the right ventricle and the left ventricle. The ultrasound probe may remain outside of the heart during this step to avoid further trauma to the heart, but under some circumstances may be inserted into a portion of the heart. The method may also comprise using the flexible and/or curved needle puncture and/or pass through the septal wall or septum into the left ventricle, e.g., at the second puncture site. The method may further comprise using the ultrasound transducer to identify a third puncture site on a posterior wall of the left ventricle. The method may also comprise extending an inner curved needle from the flexible and/or curved needle in the left ventricle and through the posterior wall. The step of treating the condition may further comprise deploying an anchor (e.g., a self-expandable anchor as described herein) through the flexible and/or curved needle or through a separate delivery catheter and placing the superior anchor in contact with an exterior surface of the heart and/or pericardium. If a delivery catheter is used, a guidewire may optionally be positioned in a desired location and the delivery catheter advanced along the guidewire.

In one embodiment, a catheter/device (e.g., a C-shaped catheter/device or puncture location catheter/device) may be used for identifying a puncture site (e.g., on a wall of a heart) during medical treatment, e.g., by causing a bend/bulge in a wall of a heart that can be viewed with an ultrasound probe or other viewing device. This may be used with any of the systems or methods described elsewhere herein. The catheter/device may comprise: a proximal handle; a positioning tube coupled with the proximal handle, the positioning tube may include an elongate portion and a curved portion, and these may be integral and/or connected together in a variety of ways, e.g., a proximal bend may be positioned between them or connect them. The curved portion may have a radius of curvature configured for extending around a portion of an organ or heart (e.g., around the left side of a heart). An elbow may be disposed at a distal end of the curved portion. The catheter/device may include a guide aligned with a longitudinal axis of the elongate portion, and may include a finger moveable relative to the guide. The elbow may be configured/designed such that the guide and/or finger are oriented and aligned with a longitudinal axis of the elongate portion. The device/catheter may also include an applicator disposed near the proximal handle, the applicator being connected to the finger via a connector that passes within a first lumen of the curved portion, such that the applicator can be manipulated to move the finger relative to the guide.

In one exemplary embodiment, alignment of the finger with the longitudinal axis of the elongate portion may be configured to help indicate a location and orientation of the finger near the posterior wall of the human heart. In one exemplary embodiment, a spring is configured to bias the finger in a retracted configuration such that a pressing force applied to the applicator compresses the spring and transitions the finger to an extended configuration, and wherein upon removal of the pressing force the spring automatically transitions the finger back to the retracted configuration. The positioning tube may comprise one or multiple lumens. A second lumen, different from the first lumen, may be configured for deploying an anchor at the puncture site during medical treatment. The catheter/device may be a C-shaped device/catheter or puncture location device/catheter as described elsewhere herein and may include any of the described features and be used in any of the described methods or steps.

BRIEF DESCRIPTION OF THE DRAWINGS

The drawings refer to embodiments of the present disclosure in which:

FIG. 7A is a side plan view of an exemplary embodiment of a trocar catheter;

FIG. 7B is a side plan view of the trocar catheter of FIG. 7A with a trocar distal tip deployed;

FIG. 7C is a cross-sectional view taken along a midline of the trocar catheter of FIG. 7A illustrating the trocar distal tip retracted into an interior lumen;

FIG. 7D is a cross-sectional view taken along a midline of a proximal handle of the trocar catheter of FIG. 7A and illustrates a plunger mechanism;

FIG. 11A illustrates an exemplary embodiment of an introducer system suitable for interventional cardiology procedures;

FIG. 11B illustrates the exemplary embodiment of the introducer system of FIG. 11A in a configuration for puncturing tissue; and FIG. 11C illustrates the exemplary embodiment of the introducer system of FIG. 11A with a guidewire being deployed through an inner lumen of the introducer system.

FIG. 12A is a perspective view of an exemplary embodiment of a C-shaped puncture location catheter/device suitable for use during medical treatment;

FIG. 12B is a side plan view of the exemplary embodiment of the C-shaped puncture location catheter/device illustrated in FIG. 12A; and FIG. 12C is a front plan view of the exemplary embodiment of the C-shaped puncture location catheter/device illustrated in FIG. 12A.

Figure 1A:
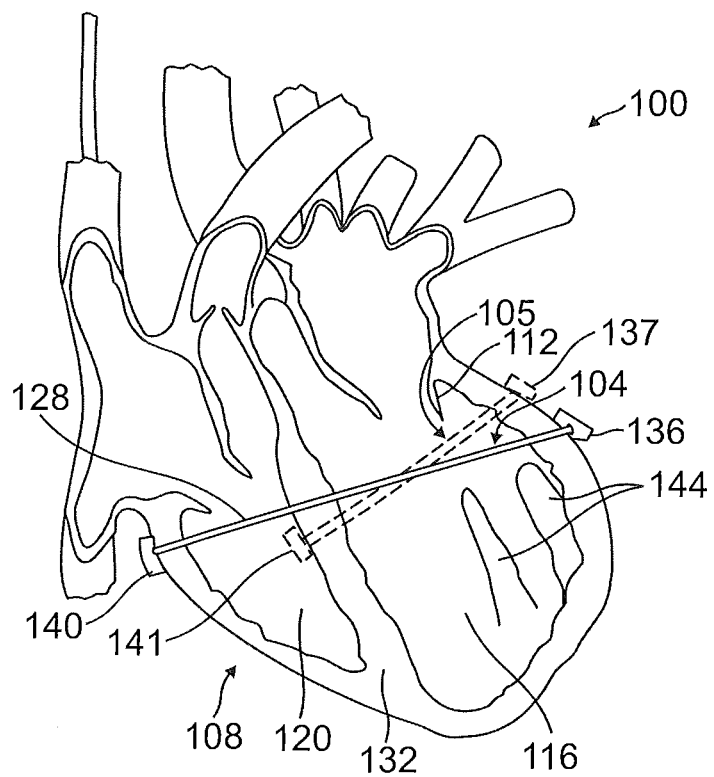
FIG. 1A is a vertical cross-sectional view of left and right ventricles of a human heart illustrating an orientation of an exemplary mitral valve splint; an alternative mitral valve splint with one anchor against the septum of the heart is also shown in outline.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

Various aspects of the present disclosure generally relate to systems, assemblies, apparatuses, devices, and methods for medical treatment and/or treating heart conditions, including, by way of example, treating dilatation, valve incompetencies (including mitral valve regurgitation), and other similar heart failure conditions. The systems, assemblies, apparatuses, devices, and methods described may be used in a variety of medical procedures and treatments. Many examples discussed herein are adapted for a transcatheter medical treatments that may not require full, open surgery, and can be minimally invasive. The treatments can use, for example, a transfemoral or transapical approach to the heart or a portion of the heart. Each apparatus or device disclosed herein preferably operates passively in that, once placed in the heart, the device does not require an active stimulus, either mechanical, electrical, or otherwise, to function. Implanting one or more of the devices of the present disclosure operates to assist in an apposition of heart valve leaflets so as to improve valve function. In addition, the devices disclosed herein may either be placed in conjunction with other devices that, or may themselves function to, alter the shape or geometry of the heart, locally and/or globally, and thereby further increase the heart's efficiency. That is, the devices disclosed herein generally facilitate an increased pumping efficiency of the heart by way of an alteration in the heart's shape or geometry and concomitant reduction in stress on heart walls, and through an improvement in valve function.

The present disclosure offers numerous advantages over existing treatments for various heart conditions, including valve incompetencies. The devices disclosed herein are relatively easy to manufacture and use, and the surgical techniques and tools for implanting the devices of the present disclosure do not require the highly invasive procedures of current surgical techniques. For instance, the treatments described herein do not require removing portions of heart tissue, nor do they necessarily require opening the heart chamber or stopping the heart during operation. For these reasons, the treatments and techniques for implanting the devices of the present disclosure convey a reduced risk to the patient as compared with other techniques. The less invasive nature of the treatments and techniques and tools of the present disclosure may further allow for earlier intervention in patients with heart failure and/or valve incompetencies.

In one embodiment, the present disclosure involves geometric reshaping of the heart and treating valve incompetencies. In certain aspects of the present disclosure, substantially an entire chamber geometry is altered so as to return the heart to a more normal state of stress. Models of this geometric reshaping, which includes a reduction in radius of curvature of the chamber walls, can be found in U.S. Pat. No. 5,961,440 incorporated above. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present disclosure reduces the stress in the walls of the heart chamber to increase the heart's pumping efficiency, as well as to stop further dilatation of the heart.

Although the present disclosure is discussed in connection with treating the mitral valve of the heart, the present disclosure may be applied to various chambers of the heart and for other valves of the heart for similar purposes. More broadly, the systems, apparatuses, methods, etc. disclosed herein may be used in other applications to change the geometries and/or stresses of other parts of the body. It also is contemplated that the present disclosure may be used to support an infarcted heart wall so as to prevent further dilatation, or to treat aneurysms in the heart. It is further contemplated that the present disclosure may be placed relative to the heart without altering the shape of the chamber, and only altering the shape of the valve itself.

In the following description, numerous specific details are set forth in order to provide a thorough understanding of the present disclosure. It will be apparent, however, to one of ordinary skill in the art that the invention disclosed herein may be practiced without these specific details. Thus, the specific details set forth are merely exemplary. The specific details may be varied from and still be contemplated to be within the spirit and scope of the present disclosure. In other instances, specific numeric references such as "first anchor" may be made. However, the specific numeric reference should not be interpreted as a literal sequential order but rather interpreted that the "first anchor" is different from a "second anchor." The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes systems, apparatuses, and related methods for medical treatment, e.g., for treatment of functional mitral valve regurgitation within a human heart and/or for transcatheter treatment. In one embodiment, an anchoring system or system for setting an anchor and/or splint may comprise an anchor for fixating a mitral valve splint within the heart. In one exemplary embodiment, the anchor may comprise a cover supported by a ring so as to assume a generally circular, flattened, or disc-shaped configuration or other configuration to contact an exterior surface of the heart, the myocardium, or the pericardium (e.g., when tensioned with a tension member connected to the center of the anchor, the anchor may be pulled from a generally circular, flattened, or disc-shaped configuration into a cone-shaped configuration). The system may include an ultrasound probe (e.g., a trans-vaginal ultrasound probe or other ultrasound probe may be used) for imaging parts of the system and parts of the body to be treated. The ultrasound probe may include a guide attached thereto for guiding various components/instruments of the system during various steps of treatment. The system may include a flexible needle formed of a hollow tube having a multiplicity of slits (e.g., S-shaped slits, C-shaped slits, V-shaped slits, zig zag slits, straight slits, parallel slits, diagonal slits, etc.) disposed along the length of the needle to navigate to and puncture heart tissue. The system may also include a trocar catheter configured for puncturing body tissue (e.g., heart tissue) without damaging other nearby tissue. The system may include an introducer system or introducer assembly for interventional cardiology procedures that may comprise an atraumatic/blunt shape introducer inside a needle catheter to protect nearby tissue within the heart during advancing a guidewire or other instrument through a lumen of the introducer. In one embodiment, these needles, catheters, trocars, introducer assemblies, etc. may be guided to a desired location using the guide attached to the ultrasound probe.

The present disclosure also describes methods for using an ultrasound probe (e.g., a trans-vaginal ultrasound probe or an ultrasound probe designed for use in treatment of mitral valve incompetency, mitral valve regurgitation, and other similar conditions) to assist during treatment of conditions of the human heart. The methods may comprise loading a medical instrument (e.g., a trocar, trocar catheter, needle, needle catheter, catheter, etc.) into a guide of the ultrasound probe. The guide may be fastened to an ultrasound probe comprising an elongate shaft extending from a proximal handle to a distal end. The ultrasound probe may be inserted into a patient by way of an incision. The distal end of the ultrasound probe may then be navigated to a location adjacent to an exterior surface of the heart and/or pericardium. A treatment site or entry site may be identified on an exterior surface of the heart and/or pericardium using an image(s) (e.g., a live/real-time image) obtained using an ultrasound transducer disposed within the distal end of the ultrasound probe. The ultrasound probe may be configured to give a wide angle of view/images. The medical instrument may be advanced using the guide to the treatment site or entry site, and the condition of the heart may be treated. The medical instrument may also be withdrawn from the treatment site or entry site. Additionally, the method may include identifying an additional treatment sites or additional treatment sites (e.g., a second treatment site on the septum and/or third treatment site on a posterior wall of the left ventricle) using an image(s) (e.g., a live/real-time image) obtained using the ultrasound transducer. The method may include using the guide on the ultrasound probe to guide the medical instrument or another, different medical instrument(s) to the additional treatment site(s) and using the medical instrument(s) at the additional treatment site(s). The ultrasound probe may remain outside of the heart when identifying the additional treatment site(s) and guiding the instruments to the additional treatment site(s) to avoid more trauma to the heart, but under some circumstances may be inserted into a portion of the heart. In one embodiment, a trans-vaginal ultrasound probe is used in one, more than one, or all of the steps recited above, and may be used for or in association with other steps described herein as well.

Use of an ultrasound probe as set forth in this disclosure can provide several advantages, including, for example, (a) the ultrasound probe may facilitate very accurate predicting/planning of a path or paths that may be used by various medical instruments during treatment (e.g., a path for a needle and/or delivery system) prior to puncturing the tissue or inserting the medical instrument; (b) ultrasound probes designed/configured to provide a wide vision angle (e.g., 120-170 degrees, about 150 degrees, etc.), when on the heart, may allow a user to image or see the whole heart (or a large portion or majority of the heart) and the coronaries; (c) ultrasound probes designed/configured to detect metal objects with minimal artifacts can make it much easier to see the guidewire, needle, DS components, and other instruments/components used during treatment; (d) medical instruments (e.g., needles, etc.) held in a guide on the ultrasound probe may be much more stable and easier to control than a freestanding instrument (e.g., the handle of the probe may be manipulated to control the instrument and may impart added stability); (e) holding medical instruments (e.g., needles, etc.) in a guide on the ultrasound probe may enable a user to image the treatment area or heart using both angiography and echocardiography simultaneously, since the user may control the instrument from a location (e.g., handle of the probe) remote from the angiography radiation; and (f) using an ultrasound probe according to this disclosure may be especially helpful in trans-apical procedures for identifying the best puncturing site (e.g., at an apex of the left ventricle of the heart) and guiding and orienting of the puncture and instruments will be much more accurate allowing the procedure to be completed more quickly and safely.

FIGS. 1A-2B illustrate an exemplary treatment area/environment 100 wherein a mitral valve splint is placed within a human heart 108. In FIGS. 1A and 1B, an exemplary mitral valve splint 104 is placed within a human heart 108 so as to lessen myocardial muscular stresses and treat leaflet apposition of a mitral valve 112, as discussed herein. FIG. 1A is a vertical cross-sectional view of left ventricle 116 and right ventricle 120 of the heart 108 illustrating an exemplary orientation of the MV splint 104 within the heart 108. An alternative MV splint 105 is shown in outline. MV splint 105 may be similar to MV splint 104 or different, but MV splint 105 is positioned with an anchor 141 against the septum 132 of the heart instead of outside the heart like anchor 140. The exact placement and orientation of MV splint 104 and MV splint 105 and their components may vary; the placements and orientations shown in FIGS. 1A-2B are non-limiting examples.

Figure 1B:
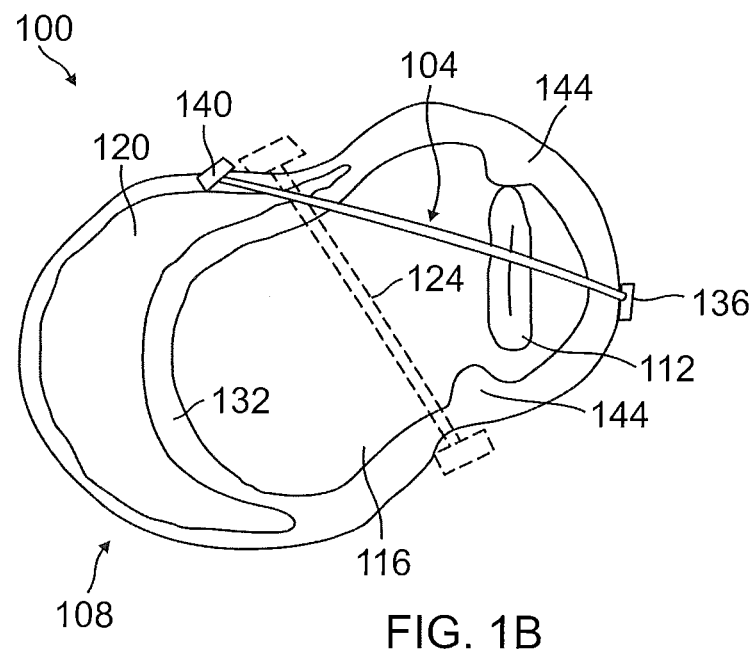
FIG. 1B is a transverse cross-sectional view of the left and right ventricles illustrating an orientation of an exemplary mitral valve splint used in combination with a transventricular splint for lessening myocardial muscular stresses and assisting in apposition of valve leaflets.

FIG. 1B shows a transverse cross-sectional view of the left and right ventricles 116, 120 illustrating an orientation of the MV splint 104 used in combination with a transventricular splint 124 (shown in outline, but may be used simultaneously with MV splint 104) for lessening myocardial muscular stresses and assisting in apposition of valve leaflets.

Figure 2A:
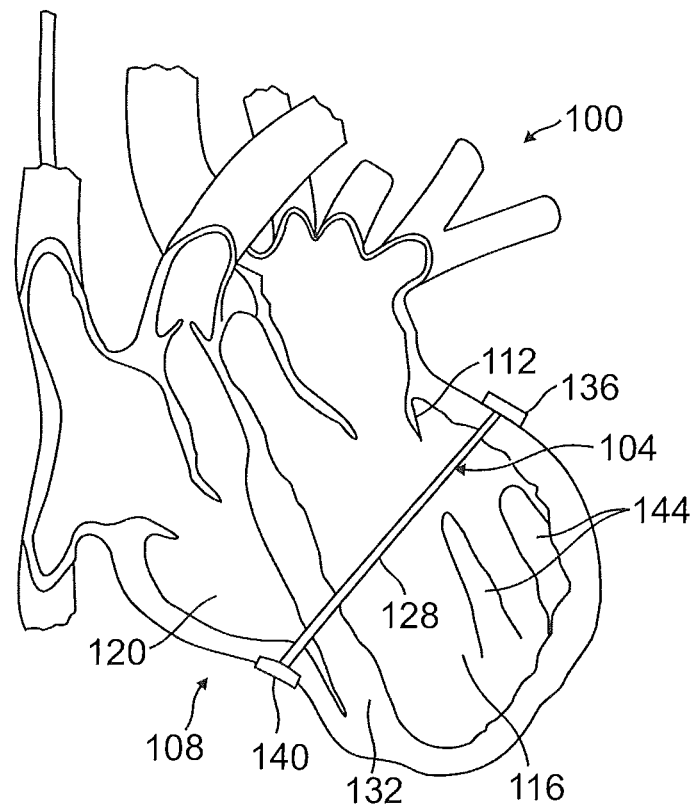
FIG. 2A is a vertical cross-sectional view of left and right ventricles of a human heart illustrating another possible orientation of an exemplary mitral valve splint.
Figure 2B:
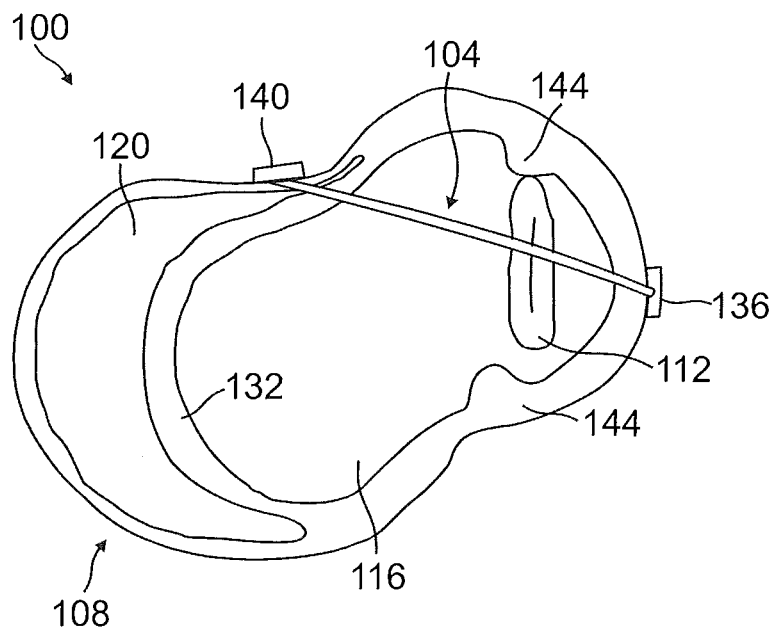
FIG. 2B is a transverse cross-sectional view of the left and right ventricles illustrating an orientation of an exemplary mitral valve splint, which may be the same as or similar to that shown in FIG. 2A.

FIGS. 2A-2B illustrate a possible orientation and placement of mitral valve splint 104 within a human heart 108 so as to lessen myocardial muscular stresses and treat leaflet apposition of a mitral valve 112, as discussed herein. FIG. 2A is a vertical cross-sectional view of left ventricle 116 and right ventricle 120 of the heart 108 illustrating an exemplary orientation of the MV splint 104 within the heart 108. FIG. 2B shows a transverse cross-sectional view of the left and right ventricles 116, 120 illustrating an orientation of the MV splint 104. Because the wall of the right ventricle is generally thinner than the wall of the left ventricle and because the blood pressure in the right ventricle is generally lower than in the left ventricle, when force is applied to the right ventricle heart wall (e.g., when the MV splint 104 is tensioned pulling anchors 136 and 140 toward each other), the wall or a portion of the wall of the right ventricle may be compressed inwardly or deformed as shown in FIGS. 2A and 2B and may even be pushed into contact with septum 132. A lower placement of anchor 140 along the right ventricle wall as shown in FIG. 2A may reduce issues associated with collapsing the right ventricle wall inwardly (e.g., this can leave the upper half of the right ventricle functioning normally or better than if the upper portion of the right ventricle was more collapsed).

A superior anchor 136 is disposed at a first end of the tension member 128 and positioned adjacent to the left ventricle 116. An inferior anchor 140 is disposed at a second end of the tension member 128 and may be positioned adjacent to the right ventricle 120 (e.g., external to the heart outside the right ventricle as shown in FIGS. 1-2) or may be positioned inside the right ventricle against a wall of the septum 132. Tension member 128 of the MV splint 104 extends from anchor 140 across the right ventricle 120, through the septum 132, and across the left ventricle 116 of the heart to anchor 136. A primary function of the MV splint 104 is to impart a shape change to an annulus of the mitral valve 112, as well as advantageously reposition papillary muscles 144. As such, the tension member 128 may extend through the heart 108 superior to the papillary muscles 144 and may be oriented primarily across the mitral valve 112 and on or below the mitral valve annulus while avoiding key vascular structures. Further details regarding specific treatments for lessening myocardial muscular stresses and leaflet apposition of the mitral valve, as well as devices and methods for delivering mitral valve splints, are disclosed in U.S. Pat. No. 7,766,812, incorporated herein above.

Figure 3A:
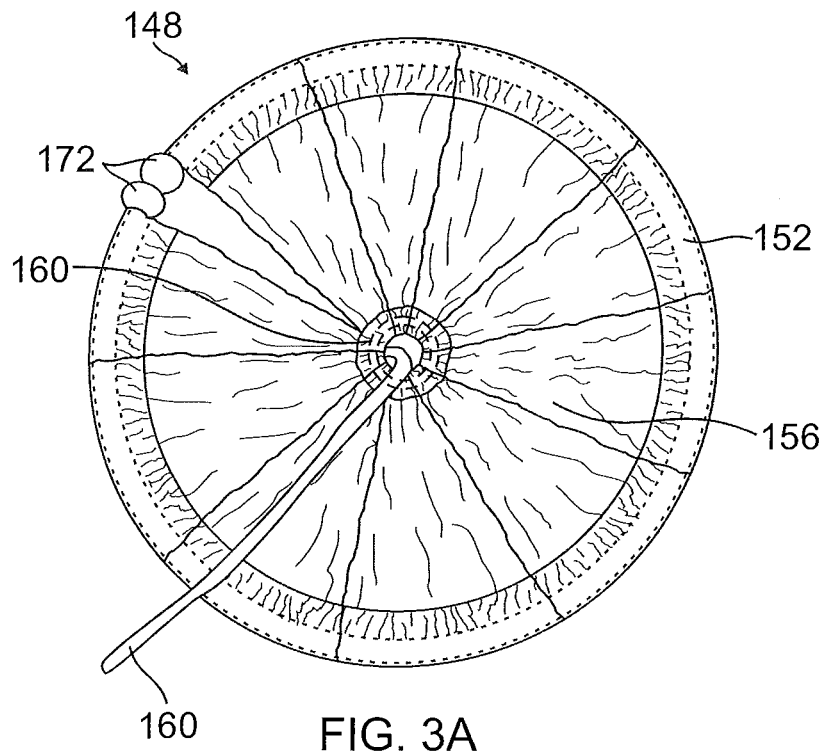
FIG. 3A illustrates an exemplary embodiment of a self-expandable anchor suitable for anchoring a mitral valve splint, the anchor having a ring in a circular configuration and a cover in a disc-shaped configuration.
Figure 3B:
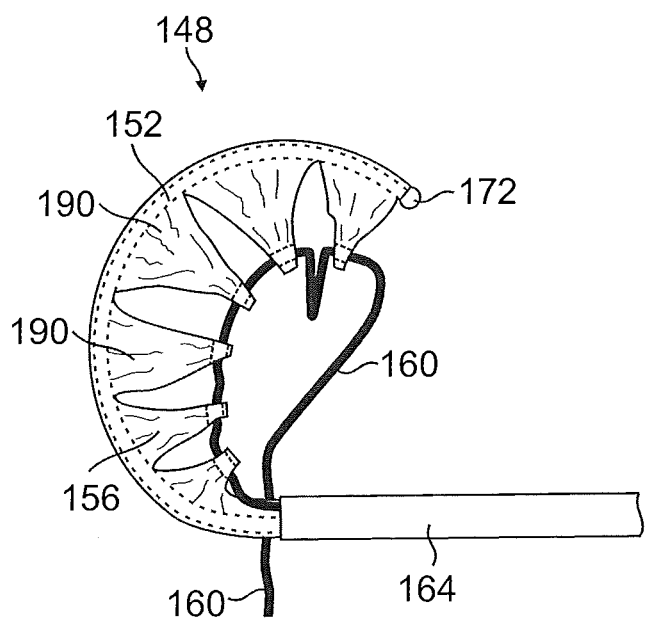
FIG. 3B illustrates the self-expandable anchor of FIG. 3A transitioning between a straightened, low-profile configuration inside a catheter and an deployed configuration.

FIGS. 3A-3B illustrate an exemplary embodiment of a self-expandable anchor 148 suitable for fixating the MV splint 104 within the heart 108, e.g., as described above. The self-expandable anchor 148 may comprise a ring 152 which peripherally supports a cover 156. Upon cinching a centrally disposed tension member or cord 160, the cover 156 can assume a disc-shaped or pie-shaped configuration, e.g., as shown in FIG. 3A. It is contemplated that the self-expandable anchor 148 may be utilized for either or both of the superior and inferior anchors 136, 140. Optionally, different types of anchors may be used for the superior and inferior anchors. As will be appreciated, the circular/disc-shaped/pie-shaped configuration of the self-expandable anchor 148 is well suited for anchoring the tension member 128 in position within the heart 108, as well as withstanding the forces encountered during changing the shape of the heart 108, as described above. In one embodiment, the circular, disc-shaped, or pie-shaped configuration provides a surface area of substantially 4 $cm^2$, which effectively eliminates migration of the anchor into the tissue of the heart 108. Optionally, the surface area may be between 2 $cm^2$ and 6 $cm^2$ or between 3 $cm^2$ and 5 $cm^2$, though other sizes are also possible. Further, the anchor 148 may preferably be configured to withstand forces due to tension within the tension member 128 of up to substantially 17 Newtons (N). A larger surface area helps the anchor withstand higher forces. For example, the embodiment shown in FIGS. 3A-3B can withstand forces of 17 Newtons with a surface area of 4 $cm^2$. As will be appreciated, the relatively large surface area of the cover 156 coupled with the centrally disposed tension member 160 provide an inherently stable configuration of the self-expandable anchor 148, thereby eliminating mechanical failures and migration into the tissue as encountered with other anchors. Further, the large surface area of the cover 156 and the centrally disposed tension member 160 cooperatively operate as a closure device which seals the punctures in the walls of the heart 108. The cover may be formed of a material that allows tissue ingrowth into the material after implantation.

As can be seen in FIGS. 3A-3B, the anchor 148 may transition between a deployed configuration (e.g., circular/disc-shaped/pie-shaped configuration) and a collapsed or low-profile configuration (.e.g., a straightened configuration) whereby the anchor may be loaded into a delivery catheter. As can be seen in FIG. 3B, the tension member 160 may be loosened to allow the cover 156 to change from the deployed configuration (e.g., flattened/disc-shaped/pie-shaped configuration or, when tensioned, cone-shaped configuration) to a collapsed or low-profile configuration whereby the cover may be folded or compressed against the ring 152. Upon extending or changing the ring 152 from a circular or ring-shaped configuration to a straightened configuration (and optionally folding the cover against the ring), the self-expandable anchor 148 may be loaded into a lumen of a catheter 164 for delivery, (e.g., into the heart 108). During delivery of the superior anchor 136 (e.g., anchor 148), the delivery catheter 164 may be pushed through the walls of the heart 108 and navigated to a suitable location outside of the left ventricle 116. Some of the steps disclosed in U.S. Pat. No. 7,766,812, incorporated above, might also be used. Upon pushing the self-expandable anchor 148 out of the lumen of the delivery catheter 164, the ring 152 may automatically change from the straightened or low-profile configuration to a deployed configuration (e.g., a circular configuration), as shown in FIG. 3B, in which the anchor 148 is transitioning between a low-profile configuration in the catheter 164 and a delivery or deployed configuration.

After initial deployment of the anchor 148 from the catheter 164, the tension member or cord 160 may be pulled, which then draws the central portion of the cover 156 taut toward the center of the ring 152, thereby producing the circular, flattened configuration or the disc-shaped/pie-shaped configuration of the cover shown in FIG. 3A (although, if pulled away from a plane aligned with the ring 152, the cover may have a more cone-like shape or configuration). Tightening the tension member 160 then pulls the self-expandable anchor 148 against the exterior surface of the heart wall, the myocardium, or the pericardium such that the cover 156 either lays flat against the surface or is tensioned such that the cover is pulled into a cone-like configuration, each with the tension member 160 passing through the puncture in the heart wall. A similar procedure may be utilized for deploying the self-expandable anchor 148 as the inferior anchor 140; however, the side of the heart having the inferior anchor is more easily accessible and a wider variety of anchors and procedures for deploying and securing the inferior anchor 140 may be used, e.g., the inferior anchor 140 may not need to assume as low a profile because it will not cross through the heart. In some embodiments, the tension member 160 passing between the superior and inferior anchors 136, 140 may comprise the tension member 128 shown in FIG. 1. Upon sufficiently tightening the tension member 160, the anchors 136, 140 are drawn inward or toward each other so as to suitably reshape the heart 108, as shown in FIGS. 1-2. The tension members described herein may be cords, wires, cables, etc. and may be rigid, semi-rigid, or flexible and may be elastic or non-elastic. An elastic tension member may allow some give (e.g., expansion and contraction) during movement or beating of the heart, but bias the heart to the desired, whereas a non-elastic tension member will maintain the same or substantially the same relative distance between the superior and inferior anchors. The tension members may optionally be braided or include a braided portion. The tension members may be formed of a high strength/high performance polymers, e.g., UHMWPE.

Figure 4:
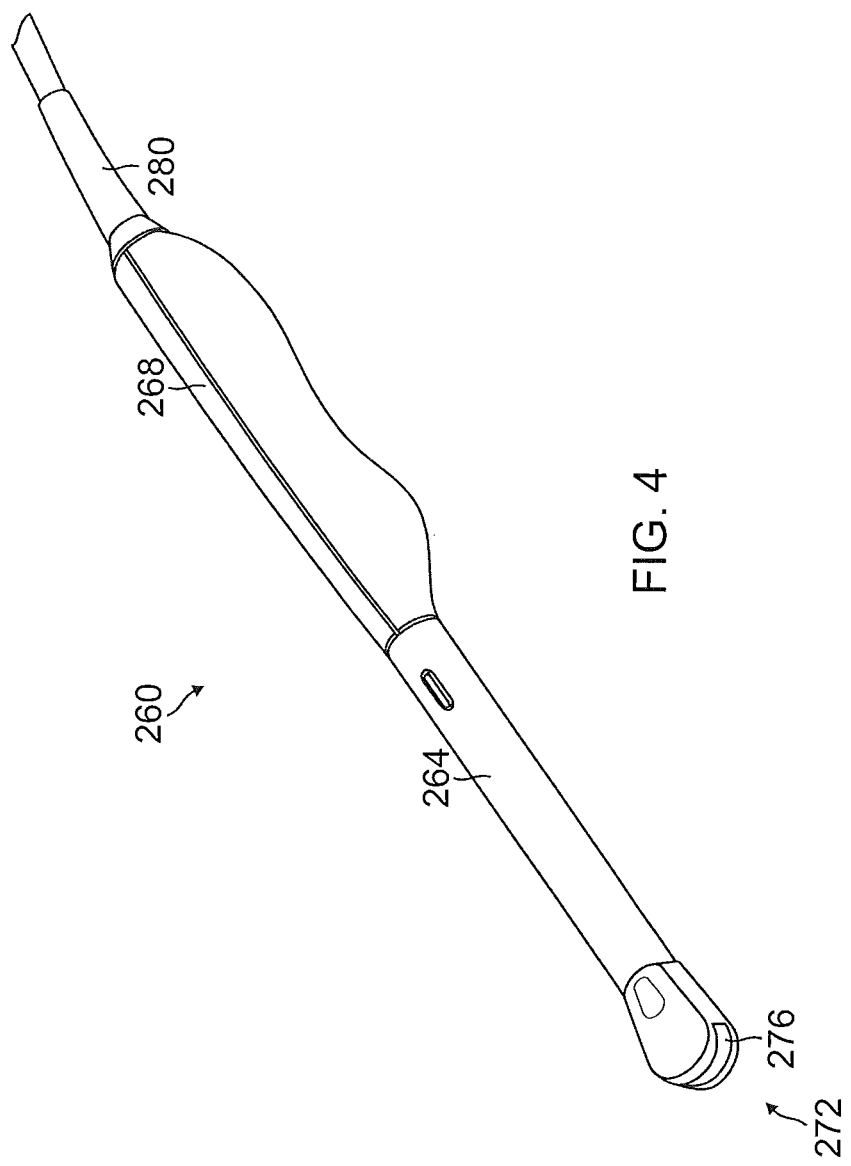
FIG. 4 is a perspective view illustrating an exemplary embodiment of an ultrasound probe for treatment of conditions within the human heart.

FIG. 4 illustrates an exemplary embodiment of an ultrasound probe 260 for treatment of various conditions within the human heart 108, according to the present disclosure. The ultrasound probe 260 may be a trans-vaginal ultrasound probe or may be a probe configured, modified, or adapted specifically for treating mitral valve issues (e.g., for treating functional mitral valve regurgitation). Treatment methods using a trans-vaginal ultrasound probe in lieu of a conventional epicardial echocardiography probe may provide greater visibility to the surgeon during puncturing the heart and may cause less trauma to the patient, thereby imparting greater benefit to the patient. Treatment methods using an ultrasound probe configured specifically for treating mitral valve issues in lieu of a conventional epicardial echocardiography probe may provide similar benefits (e.g., greater visibility to the surgeon during puncturing the heart and less trauma); however, these ultrasound probes may be configured to have additional benefits as well, e.g., these may be better shaped and sized for mitral valve procedures, may be more flexible, may have a repositionable distal end, and/or may have other features beneficial for mitral valve treatment. The ultrasound probes and ultrasound systems/assemblies described herein may be used for imaging, viewing, and guiding the various medical instruments and regions of the body described herein during the methods, steps, and/or treatments described herein.

As shown in FIG. 4, the ultrasound probe 260 may comprise an elongate shaft 264 extending from a proximal handle 268 to a distal end 272 of the probe. An ultrasound transducer 276 may be disposed within the distal end 272 in a longitudinal orientation so as to facilitate viewing tissue and structures directly in front of the distal end during operation of the probe. A cable 280 may house or enclose electrical wires extending from the ultrasound transducer 276 and through the elongate shaft 264 and the handle 268, for communicating electrical signals between the transducer and other equipment of an ultrasound processing and imaging system (e.g., a computer, processor, memory, display, speakers, software, hardware, and/or other components). As shown in FIG. 4, the ultrasound probe 260 may comprise generally smooth exterior surfaces and contours configured to minimize or limit damaging tissues and structures within the patient (e.g., along the path to the heart and/or within the heart).

The ultrasound probe 260 (e.g., a trans-vaginal ultrasound probe or an ultrasound probe designed for use in treatment of mitral valve incompetency, mitral valve regurgitation, and other similar conditions) is significantly narrower than conventional epicardial echocardiography probes. The embodiment of the ultrasound probe 260 illustrated in FIG. 4 may have a diameter which is approximately 2 centimeters (cm) or more smaller than the diameter of conventional epicardial echocardiography probes, and thus the ultrasound probe 260 may be inserted into a relatively small access point in a patient for monitoring of the heart 108 during advancement of a catheter, a trocar, or other medical instrument as described herein. In one embodiment, the diameter of the transducer 276, distal end 272, and/or shaft 264 is 1 inch or about 1 inch; however, the diameters of the transducer 276, distal end 272, and/or shaft 264 may vary and be within the range of 0.25 inches to 2 inches, the range of 0.5 inches to 1.5 inches, or 0.7 inches to 1.2 inches. In treating mitral valve incompetency, mitral valve regurgitation, and other conditions of the heart, the ultrasound probe 260 may be inserted into the access point (e.g., incision, puncture, opening, etc.) into the body and then advanced toward an exterior surface of the heart and/or pericardium (e.g., in the region outside the right ventricle of the heart 108). The ultrasound probe 260 may be advanced into the access point and between ribs, if necessary. With the distal end 272 positioned directly adjacent to the heart wall and/or pericardium, the ultrasound transducer 276 provides the surgeon with a direct view of the heart wall and/or pericardium, thereby facilitating determining a treatment site and accurately positioning a puncture/incision in the heart wall.

It is contemplated that in some embodiments, the elongate shaft 264 and/or distal end 272 may be configured to flex, bend, articulate, and/or otherwise change the orientation of the ultrasound transducer 276, whereby the surgeon may be able to change the orientation of the distal end 272 so as to view more areas of the heart (e.g., in directions other than straight ahead). It is further contemplated that the ultrasound system may comprise one or more actuators to enable the surgeon to flex, bend, articulate, and/or otherwise change a portion of the ultrasound probe (e.g., to alter the orientation of the ultrasound transducer 276), and thus to navigate the distal end 272 within the patient and image all the desired regions and directions. Steps involving navigating and/or imaging may include flexing, bending, articulating, and/or otherwise changing a portion of the ultrasound probe (e.g., the shaft) to better navigate the ultrasound probe to a desired location and/or to alter the orientation of the ultrasound transducer 276 for better imaging of a desired location. This may be done using the one or more actuators.

Figure 5:
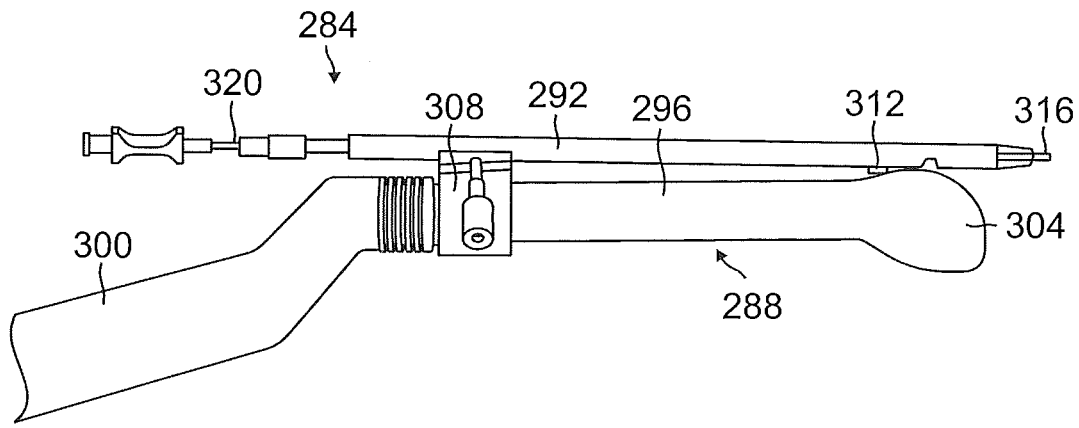
FIG. 5 is a side elevation view illustrating an exemplary embodiment of an ultrasound probe system or assembly having an ultrasound probe with an attached guide.

FIG. 5 is a side elevation view illustrating an exemplary embodiment of an ultrasound probe system or assembly 284 comprising an ultrasound probe 288 and an exemplary guide 292. The ultrasound probe 288 may include features the same as or similar to the ultrasound probe 260 described above. For example, the ultrasound probe 288 may comprise an elongate shaft 296 that extends from a proximal handle 300 to a distal end 304. Also, an ultrasound transducer, such as the transducer 276, may be housed within the distal end 304. The ultrasound transducer may be configured to provide a view of tissues and structures directly in front of the distal end 304 during operation of the ultrasound probe system/assembly 284.

The guide 292 may include an enclosed lumen through which the medical instrument(s) pass as they are guided to a desired location. The guide 292 may optionally not include a lumen, but include other features to guide the medical instrument(s), e.g., loops or rings through which the medical instrument passes, side walls, and/or other features. The guide 292 may be attached/fastened to the ultrasound probe 288 by way of a proximal coupling 308 and a distal coupling 312 such that the guide is parallel to the elongate shaft 296 and a distal end 316 of the guide is adjacent to the distal end 304 of the probe. While couplings 308 and 312 as shown in FIG. 5 provide examples of how the guide 292 may be attached/fastened to the ultrasound probe 288, the guide 292 may be attached/fastened to the ultrasound probe 288 in other ways as well, e.g., screws, ties, adhesion, locking mechanisms, etc. A medical instrument 320 (e.g., a needle, catheter needle, or other medical instrument) may be disposed within the guide 292 such that the medical instrument 320 may be used to puncture tissue adjacent to the distal end 304 and in direct view of the ultrasound transducer. The proximal coupling 308 may be a mechanical fastener which receives and engages a portion of the ultrasound probe 288 or the entire circumference of the ultrasound probe 288. The distal coupling 312 may comprise a mechanical fastener as well. In one embodiment, the distal coupling 312 may comprise small tab which engages with a small loop or slot disposed on the guide 292. The distal coupling 312 may be configured to hold the guide 292 closely against the ultrasound probe 288 so as to facilitate passing the probe and the guide into a relatively small access point, entry point, incision, puncture, etc. in the patient.

Figure 6:
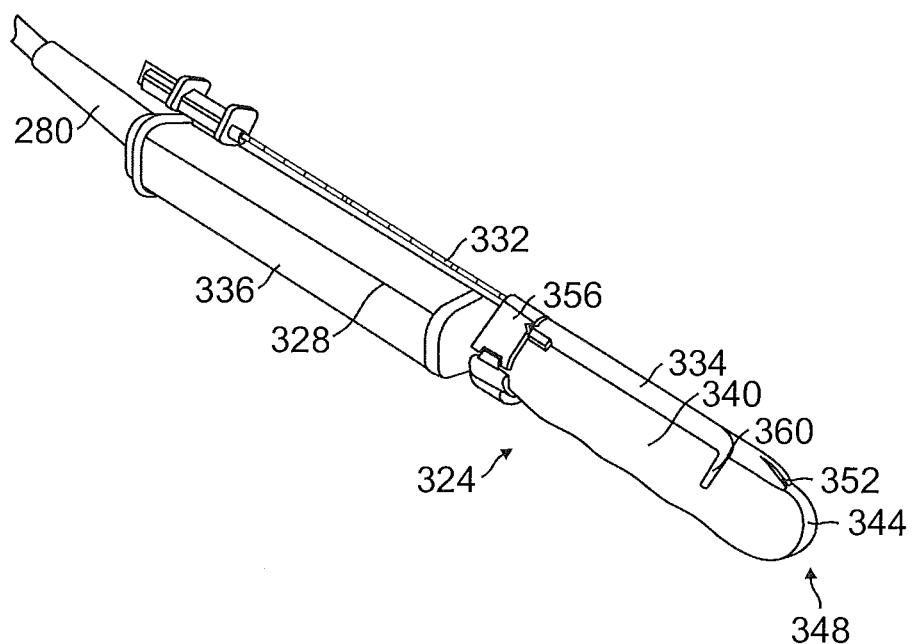
FIG. 6 is a perspective view illustrating another exemplary embodiment of an ultrasound probe system or assembly having an ultrasound probe with an attached guide.

It should be recognized that the ultrasound probe need not be limited to the specific shapes illustrated in FIGS. 4-5, nor should the proximal and distal couplings 308, 312 be limited to those shown in FIG. 5. Accordingly, FIG. 6 illustrates an exemplary embodiment of an ultrasound probe system or assembly 324 comprising an ultrasound probe 328 and a guide 334 which supports a medical instrument 332 (e.g., a needle, needle catheter, or other instrument), according to the present disclosure. The ultrasound probe 328 may be similar to the probes 260, 288 and include the same or similar features, with the exception that the ultrasound probe 328 has somewhat different shapes and orientations between the various components comprising the probe 328. A proximal handle 336 of the ultrasound probe 328 may be generally cylindrical and suitably sized for grasping during operation of the ultrasound probe system/assembly 324. Distal of the proximal handle 336 may be an elongate shaft 340. Elongate shaft 340 may have a diameter that is the same as or relatively smaller than the diameter of the proximal handle. As will be appreciated, the diameter of the elongate shaft 340 may be advantageously sized and configured for extending into the access point in the patient, as described herein. Further, any of various textures, surface shapes, or features may be disposed on the elongate shaft 340, as deemed surgically appropriate, without deviating beyond the spirit and scope of the present disclosure.

As illustrated in FIG. 6, an ultrasound transducer 344 is disposed within a distal end 348 of the elongate shaft 340. The ultrasound transducer 344 may be the same as, substantially identical to, or different from the ultrasound transducer 276, illustrated in FIG. 4, and may be oriented within the distal end 348 so as to provide a view of tissues and structures directly in front of the distal end 348 during operation of the ultrasound probe system/assembly 324. A distal end 352 of the guide 334 may include an opening and may be positioned adjacent to the distal end 348 of the ultrasound probe 328. The position of the distal end 352 of guide 334 and its ability to direct the medical instrument relative to the distal end 348 of the probe may enable the surgeon to advantageously view target tissues and structures while advancing the medical instrument 332 (e.g., a needle) during treatment (e.g., during puncturing).

The guide 334 is fastened to the ultrasound probe 328 by way of a proximal coupling 356 and a distal coupling 360. The proximal coupling 356 is substantially similar to the proximal coupling 308, with the exception that the proximal coupling 356 is specifically configured to interconnect the guide 334 and the ultrasound probe 328. The distal coupling 360 is configured to engage with a portion of the circumference of the elongate shaft 340 so as to position the distal end 352 of the catheter needle 332 directly adjacent to the distal end 352, as described above. It should be understood that the proximal coupling 356 and the distal coupling 360 attach the guide 334 directly adjacent to the elongate shaft 340 so as to facilitate passing the ultrasound probe system/assembly 324 directly through the access point in the patient.

It should be understood that the ultrasound probe systems/assemblies 324, 284 are not to be limited to being operated, respectively, with the medical instruments 332, 320 of a particular type (e.g., a needle), but rather a wide variety of medical devices may be used in conjunction with the ultrasound probe systems/assemblies 324, 284, without limitation, and without deviating beyond the spirit and scope of the present disclosure. For example, in some embodiments, either of the medical instruments 332, 320 may be comprised of a trocar catheter (e.g., trocar catheter 200 of FIGS. 7A-8C), a flexible needle (e.g., flexible needle 43 of FIGS. 9 & 10), and/or an introducer system/assembly (e.g., introducer system/assembly 500 of FIGS. 11A-11C). In on embodiment, the ultrasound probe systems/assemblies 324, 284 may be used to advance the trocar catheter 200 to the heart 108. With the trocar distal tip 220 positioned within the interior lumen 202, unwanted damage to surrounding tissues and structures is prevented while the trocar catheter 200 is moved toward the heart. Once an advantageous puncture site on the heart is identified by way of either of the ultrasound transducers 344, 276, the trocar distal tip 220 may be deployed to puncture the heart and then withdrawn into the interior lumen 202 to prevent damage to surrounding tissues.

Moreover, in some embodiments, the ultrasound probe systems/assemblies 324, 284 may be coupled with any of various introducer systems, introducer assemblies, needle catheters, etc. such as flexible curved needles or various Veress-type needles, suitable for passing into the heart 108 during treatment of mitral valve incompetency, mitral valve regurgitation, and other conditions of the heart. For example, either of the ultrasound probe systems/assemblies 324, 284 may be used to provide a direct, longitudinal view of a puncture site as a needle catheter is advanced, e.g., across the right ventricle of the heart, passed through the septal wall, extended across the left ventricle, and/or passed through the posterior wall of the left ventricle.

The ultrasound probe systems/assemblies 324, 284 may also be used for fixating the MV splint 104 within the heart 108, as described in connection with FIGS. 1-2. Preferably, at least one of the superior and inferior anchors 136, 140 comprises the self-expandable anchor 148 discussed with reference to FIGS. 3A-3B. For example, during delivery of the superior anchor 136, either of the ultrasound probe systems/assemblies 324, 284 may be used to directly observe and/or guide the deployment of the self-expandable anchor 148 and to verify that the anchor assumes the ring-shaped configuration upon being extracted from the catheter outside of the left ventricle 116. As discussed with reference to FIG. 3A, the cord 160 may be pulled tight to expand the cover 156 into the disc-shaped or pie-shaped configuration and pull the anchor against the exterior surface of the heart wall. As will be recognized, either of the ultrasound probe systems/assemblies 324, 284 may be also utilized in deployment of the inferior anchor 140. Then the tension member 160 may be sufficiently tightened/tensioned between the anchors 136, 140 to suitably reshape the heart 108, as shown in FIGS. 1-2 and/or to treat mitral valve problems/incompetencies.

The ultrasound probe systems/assemblies described herein (e.g. systems/assemblies 324, 284) and any associated features and/or steps may be used in a variety of medical procedures and/or for treating various conditions of the heart. One example may include using the systems/assemblies described herein in procedures to replace at least one native valve within the heart using a prosthetic valve (e.g., a prosthetic mitral valve and/or a prosthetic aortic valve) so as to treat valve incompetencies. Delivery of the prosthetic mitral valve or the prosthetic aortic valve may be accomplished in various ways. For example, the prosthetic valve (e.g., a prosthetic mitral valve or prosthetic aortic valve) may be delivered by way of a transapical approach whereby access to the heart (e.g., left ventricle) is achieved through an incision in the chest and an incision in the apex of the heart. Alternatively, the prosthetic valve may be delivered by way of a transatrial approach through the left atrium. The transatrial approach may be performed by way of an incision in the chest and an incision through the atrial wall of the heart. It should be appreciated that any of the ultrasound probe systems/assemblies (e.g., systems/assemblies 324, 284) may be used to provide a direct, longitudinal view of each site where an incision is performed during medical treatment and/or during accessing the interior of the heart and may be used to guide a medical instrument (e.g., a needle, cutting instrument, catheter, delivery device) in a desired direction. The ultrasound probe may give a wide angle of view and allow the medical practitioner to use a guide to align the medical instrument more accurately with a desired target location. The systems/assemblies may be similarly used in other medical procedures that use a transapical or transatrial approach.

FIGS. 7A-8C illustrate an exemplary embodiment of a trocar catheter 200 configured for puncturing tissue. The trocar catheter 200 may be part of an anchoring system or system for setting an anchor, and may be usable with the ultrasound probes and/or ultrasound probe systems/assemblies described herein. e.g., to view the trocar catheter or a portion thereof during treatment. A guide (e.g., the same as or similar to guides 292, 334) may be used to insert and guide the trocar catheter 200 to a desired location or treatment site. The trocar catheter 200 may generally comprise an elongate cannula 204 having a distal end 208 and a proximal handle 212. As will be appreciated, the cannula 204 may comprise a hollow interior lumen 202 which may contain a trocar 216. The trocar 216 may comprise a trocar shaft and a trocar distal tip 220. The trocar shaft may be rigid, semi-rigid, or flexible (e.g., to make navigation to the desired location easier) and may have a lumen therethrough. The trocar 216 or trocar shaft may extend from the proximal handle 212 to a trocar distal tip 220. The proximal handle 212 facilitates a surgeon advancing the trocar distal tip 220 beyond the distal end 208, as shown in FIG. 7B, during puncturing of tissue. The handle may include controls (e.g., a lever, button, switch, sliding mechanism, plunger, etc.) for causing the distal tip 220 of the trocar to extend from the distal end of the cannula 204 for puncturing tissue and/or for causing the distal tip 220 to retract into the lumen of the cannula 204 to prevent damage to tissue from the trocar. FIG. 8B is a close-up view of the trocar distal tip 220 extending beyond the distal end 208, as shown in FIG. 7B, in accordance with the present disclosure.

FIG. 7D is a cross-sectional view, taken along a midline of the proximal handle 212, that illustrates controls, e.g., including a plunger mechanism 224, that enable the surgeon to deploy the trocar distal tip 220 during puncturing of tissue and then withdraw or retract the trocar distal tip into the distal end 208, as shown in FIG. 7C. FIG. 8C corresponds to the region in the dotted circle shown in FIG. 7C and is a close-up view of the trocar distal tip 220 positioned within the interior lumen 202, proximal of the distal end 208. As will be appreciated, withdrawing the trocar distal tip 220 into the lumen 202 in the distal end 208 of the cannula 204 prevents unwanted damage to surrounding tissues during delivery of the trocar catheter 200. In the embodiment illustrated in FIGS. 7A-7D, the trocar catheter may comprise an actuator 228 configured to deploy the trocar distal tip 220, as shown in FIG. 7B. The actuator 228 may be part of or work with the plunger mechanism 224. The plunger mechanism 224 may comprise a spring 232 that biases the trocar distal tip into the retracted position, i.e., the position in which the distal tip 220 is retracted into the lumen 202 in the distal end 208. If a spring 232 is used, the distal tip 220 may automatically retract into the lumen 202 or into the distal end 208 when the surgeon releases the actuator 228. The actuator 228 may connect (directly or indirectly) to a proximal end of the trocar 216 and may be pushed toward the distal end 208 of the cannula 204 to cause the distal tip 220 of the trocar to extend out from the lumen 202. In FIG. 7D, the distal end of the actuator 228 is shown as aligned with another component or plunger 226 having a ridge or lip on an outer surface thereof that contacts the proximal end of the spring 232. The component or plunger 226 having the ridge or lip may also include a lumen through which a shaft of the trocar 216 may pass. In one embodiment, the distal end of the actuator 228 may push against the component having the ridge or lip and may thereby compress the spring 232 to allow the distal tip 220 of the trocar 216 to move distally and extend out from the lumen 202 and distal end 208 of the cannula. When the actuator 228 is released, spring 232 may then cause the component having the ridge or lip to move proximally and thereby push the actuator proximally to cause the distal tip 220 to move proximally into the lumen 202 and distal end 208. Other controls for moving the trocar between the extended and retracted positions are also possible. A lock may be used to hold the trocar in either the extended or retracted position.

Figure 8A:
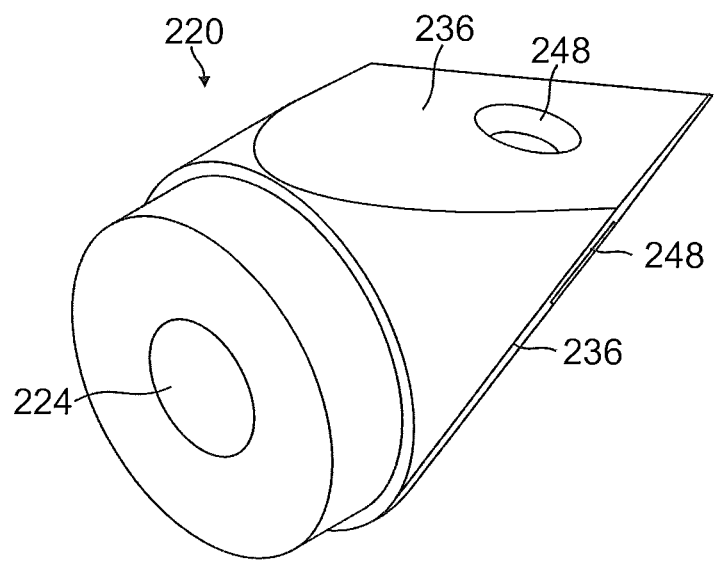
FIG. 8A is a perspective view illustrating an exemplary embodiment of a trocar distal tip.
Figure 8B:
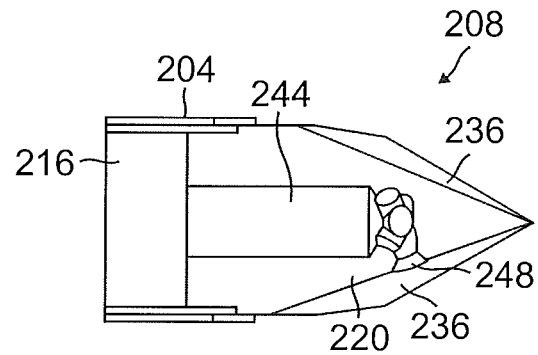
FIG. 8B is a close-up cross-sectional view of the trocar distal tip in a deployed configuration, e.g. as in FIG. 7B.
Figure 8C:
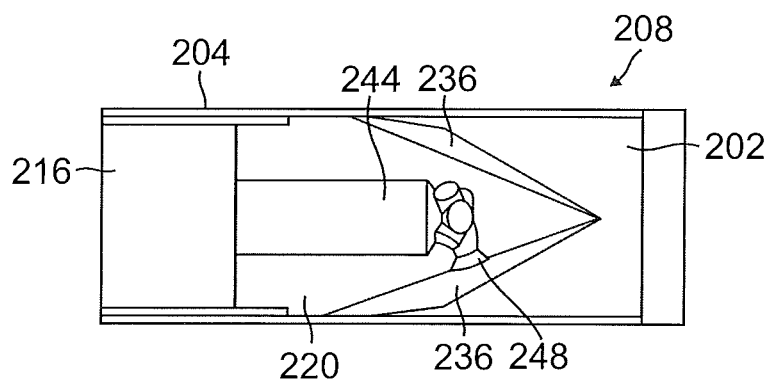
FIG. 8C is a close-up cross-sectional view of the trocar distal tip in a retracted configuration, e.g. as in FIG. 7C.

FIG. 8A is a perspective view of the trocar distal tip 220 in accordance with the present disclosure. The trocar distal tip 220 may comprise one or more surfaces 236 to form a sharpened or a puncture tip, e.g., the distal tip 220 may have one, two, three, four, five, six, or more surfaces 236. The surfaces 236 may be formed/manufactured by grinding or milling the surfaces 236, e.g., the surfaces 236 may each correspond to a grinding plane. In FIGS. 8A-8C, the distal tip 220 is shown as having been ground or milled to form three grinding plane surfaces 236 that meet to form a sharp tip. The actuator 228 may be rotatable so as to enable the surgeon to turn the surfaces 236 of the trocar distal tip 220 during tissue puncturing. Further, the trocar distal tip 220 may comprise a lumen 244 in fluid communication with one or more ports 248 disposed on one or more or all of the surfaces 236. The lumen 244 and ports 248 may be configured for contrast injection therethrough during or after tissue puncturing.

Figure 9:
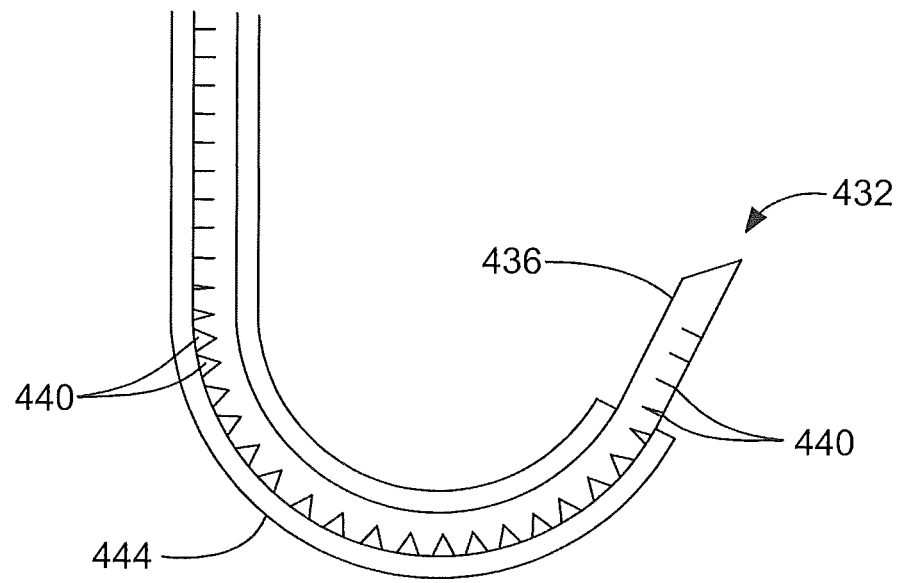
FIG. 9 illustrates an exemplary embodiment of a flexible needle.
Figure 10:
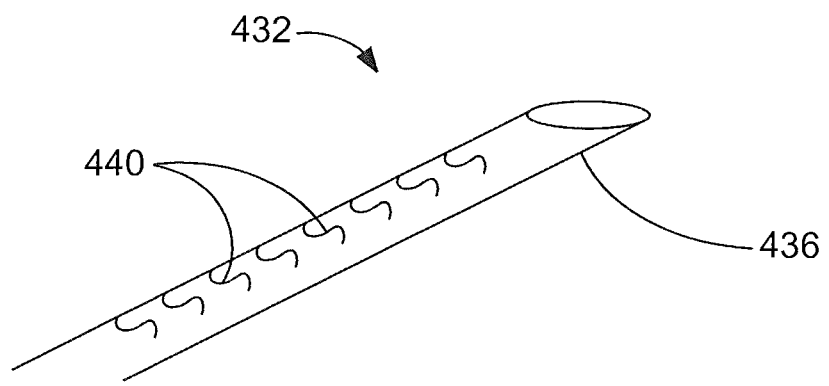
FIG. 10 is a close-up view of a distal portion of an exemplary embodiment of a flexible needle similar to the needle illustrated in FIG. 9.

FIGS. 9-10 illustrate exemplary embodiments of a flexible needle 432 that may be loaded into a guide of an ultrasound probe. The flexible needle 432 may be part of an anchoring system or system for setting an anchor, and may be usable with the ultrasound probes and/or ultrasound probe systems/assemblies described herein. e.g., to view the flexible needle 432 during treatment. A guide (e.g., the same as or similar to guides 292, 334) may be used to insert and guide the flexible needle 432 to a desired location or treatment site. The flexible needle 432 may generally comprise a hollow, shape memory tube 436 having a multiplicity of slits 440 disposed along the full length of the needle or along a portion of the needle (e.g., a distal portion of the needle). The shape memory tube 436 may be constructed of Nitinol, a shape memory alloy, or another suitable material. The slits 440 may be of a variety of shapes/configurations, e.g., S-shaped slits, C-shaped slits, V-shaped slits, zig zag slits, straight slits, curved slits, parallel slits, diagonal slits, etc. FIG. 10 is a close-up view of an exemplary flexible needle 432 showing slits 440 as S-shaped slits along a distal portion of the needle. The slits may be along different portions of the tube, e.g., FIG. 9 shows the slits 440 on the same side as the point of the beveled or sharpened tip of the needle, whereas FIG. 10 shows the slits 440 on the side of the needle opposite the point of the beveled or sharpened tip of the needle. In one embodiment, slits 440 may appear alternating on opposite sides of the needle or appear at varying locations around the needle (e.g., spaced apart in a helical shape around the needle) so the needle can more readily flex in more than one direction. The slits 440 allow the flexible needle 432 to undergo sharp turns, e.g., if delivered inside a flexible or curved catheter 444 as shown in FIG. 9, but allow the flexible needle 432 to resume a straightened configuration when extracted or pushed from the catheter 444, as shown in FIG. 10. Preferably, the flexible needle 432 is capable of turns of greater than 90 degrees having a relatively small radius. Further, the slits 440 provide a degree of rigidity to the flexible needle 432 in the straightened configuration, as well as allowing a surgeon to change the orientation of the tip of the needle 432 by rotating a proximal end of the needle extending from the catheter 384 and/or from a guide on an ultrasound probe. Thus, the flexible needle 432 is well suited to track in tortuous paths, and enables the surgeon to puncture tissue in a direction which may differ from a previous penetration direction.

In some embodiments the flexible needle 432 may be used to deliver devices by way of the hollow tube 436, such as guidewires or small diameter catheters or needles. In some embodiments, the hollow tube 436 may be used to measure pressure where the distal tip of the needle is located. In some embodiments the flexible needle 432 may be utilized as a guidewire during interventions lacking direct visibility. For example, the flexible needle 432 may be used during percutaneous cardiology or radiology interventions, using ultrasonic, angiogram, and/or fluoroscopy imaging modalities, such as during left ventricle remodeling procedures for treating functional mitral regurgitation, e.g., as described herein. During left ventricle remodeling, for example, the flexible needle 432 may be delivered through a catheter or guide (e.g., guide 292, 334) to the right ventricle 120 of the heart 108 and then oriented toward the septum 132 with a desired orientation. Upon the penetrating the septum 132 and entering the left ventricle 116, the flexible needle 432 resumes the straightened configuration illustrated in FIG. 10. In the straightened configuration, the flexible needle 432 may be oriented toward a desired puncture site on the posterior wall of the left ventricle 116, and this may be done while imaging the posterior wall and needle 432 using one of the ultrasound probes or ultrasound probe systems/assemblies described herein. In those instances wherein an additional orientation is required, however, the surgeon may manipulate or rotate the proximal end of the flexible needle 432 so as to orient the flexible needle toward the desire puncture site.

FIGS. 11A-11C illustrate an exemplary embodiment of an introducer system or introducer assembly 500 suitable for interventional cardiology procedures. The introducer system/assembly 500 may be included as part of the anchoring systems or systems for setting an anchor described herein, and may be usable with the ultrasound probes and/or ultrasound probe systems/assemblies described herein. e.g., to view the introducer system/assembly or a portion thereof during treatment. A guide (e.g., the same as or similar to guides 292, 334) may be used to insert and guide the introducer system/assembly 200 to a desired location or treatment site. The introducer system/assembly 500 may comprise a needle or needle catheter 504 and an introducer 508 disposed within an inner lumen of the needle catheter 504. The needle catheter 504 may comprise a beveled edge 512 or other sharpened edge/tip suitable for puncturing tissue. As shown in FIG. 11A, the introducer 508 may be disposed within the needle catheter 504 such that a portion of the introducer 508 extends distally beyond the beveled edge 512. The distal portion of the introducer 508 may comprise an atraumatic and/or blunt shape (e.g., rounded, partially rounded, flat, etc.) so as to operate as an atraumatic distal end of the introducer system 500 during delivery of the needle catheter 504 to the site of a puncture, as well as removal therefrom.

A spring or other biasing mechanism (not shown) may be included as part of the introducer system/assembly 500. The spring or other biasing mechanism maintains/biases the introducer 508 such that a distal portion of the introducer extends distally beyond the beveled edge 512, e.g., as shown in FIG. 11A. Upon applying pressure to the introducer 508, such as due to pushing the needle catheter 504 distally against a tissue, the introducer may be pushed/slid proximally into the needle catheter 504, thereby exposing the beveled edge 512 or other sharpened edge/tip as shown in FIG. 11B. Once exposed, the beveled edge 512 is suitable for puncturing tissue, such as muscle tissue, so as to provide access to a cavity or structure. e.g., in the heart. The introducer 508 returns to the distally extended position shown in FIG. 11A upon entering into the cavity, thereby preventing the beveled edge 512 from damaging sensitive structures within the cavity or nearby tissues. It is contemplated that in some embodiments, springs exhibiting different degrees of spring force may be incorporated into the introducer system/assembly 500, and thus the springs may be selected according to a known level of force required to penetrate a particular tissue (e.g., to prevent tissue puncture in some tissues, but allow tissue puncture in other harder tissue). Further, in some embodiments, the introducer system/assembly 500 may include a lock or locking feature that allows the introducer 508 be locked into the distally extended position so as to enable pushing against tissue without the beveled edge 512 puncturing the tissue, e.g., by preventing the introducer 508 from moving proximally in the needle catheter.

The introducer system/assembly 500 may also include a guidewire 516. The introducer 508 may comprise an inner lumen which accommodates a guidewire 516. As shown in FIG. 11C, the inner lumen in the introducer 508 facilitates advancing the guidewire 516 without requiring the introducer 508 to be withdrawn from the needle catheter 504. Thus, the inner lumen enables the guidewire 516 to be advanced while the introducer 508 protects adjacent tissues from damage from the beveled edge 512. Further, the inner lumen enables the needle catheter 504 and the introducer 508 to be retracted together from the tissue or cavity while the guidewire 516 is left remaining in the deployed position. As will be appreciated, delivery of the guidewire 516 through the inner lumen of the introducer 508 substantially eliminates injury to nearby structures and tissue that might otherwise occur due to the presence of the beveled edge 512 in absence of the introducer. Further, having a lumen through the introducer 508 saves time and the extra step of having to retract the introducer 508 or a similar component from the needle catheter prior to advancement of a guidewire or other instruments therethrough.

FIGS. 12A-12C illustrate an exemplary embodiment of a device 700 suitable for use during medical treatment and the methods described herein and which may be part of one or more of the systems described herein. The device/catheter 700 may be formed as a C-shaped device or catheter. The device/catheter 700 may be a puncture location device or puncture location catheter, and may be a multipurpose device that helps identify a puncture location, facilitates deployment of one or more anchors, and/or performs other functions. The device/catheter 700 may be included as a part of an anchoring system, as described herein. The device/catheter 700 may be used in a variety of treatments, including treating organ dilation and functional mitral valve regurgitation (FMR), as described herein. For example, the device/catheter 700 may be used as puncture location device/catheter to identify a desired puncture location and/or guide puncturing devices to create a puncture in the desired puncture location, e.g., a desired puncture location on a wall of an organ. For example, device/catheter 700 may be used to identify a puncture location and guide a puncturing device to location on a wall of a left ventricle of a heart and/or a posterior wall of the heart 108 that avoids or minimizes damage to the papillary muscles 144 or other vessels, tissue, etc., during medical treatment.

The device/catheter 700 may include a proximal handle 702, a positioning tube 704, and/or other features. Proximal handle 702 may facilitate gripping and moving the device/catheter 700. Proximal handle 702 may facilitate navigating the device/catheter 700 through an incision site and to a desired location. This may include navigating the device/catheter 700 around a portion of the heart or another organ, to a desired location/position. For example, proximal handle 702 may be used to direct/navigate the distal end of the device/catheter 700 around the region of a heart including the left ventricle 116 so as to position a distal end/region of the device/catheter 700 at a desired location along a wall of the heart (e.g., at a desired puncture location for puncture through the heart wall or a wall of the left ventricle). The device/catheter 700 may be used to help locate/identify a location outside a posterior side of the human heart 108 (e.g., a location along the posterior wall of the left ventricle at which puncturing would avoid or limit damage to blood vessels, papillary muscles, etc.). Pressing a portion of the device/catheter 700 (e.g., a guide portion 724 and/or a finger 706) into and/or moving the portion along a wall (e.g., posterior wall) of the human heart 108 (or another organ or portion of the body) may cause a bend or bulge in the wall of the heart (or other organ or portion of the body) that is detectable/viewable by way of an epicardial echo probe/ultrasound probe/another imaging device (e.g., any of the imaging devices described in this disclosure). The device/catheter 700 may thereby enable a surgeon to identify a location on an organ, heart, or portion of the body that is suitable for being punctured during medical treatment (e.g., during FMR treatment) without causing undue damage (e.g., avoiding undesired damage to vessels, papillary muscles, and/or tissue structures within the left ventricle 116 of a heart).

In the embodiment illustrated in FIGS. 12A-12C, the device/catheter 700 includes a positioning tube 704. Positioning tube 704 can be formed and configured as a generally long, thin tube having a shape suitable for being directed into an incision site and navigated around a portion of a heart or other organ to a desired location, e.g., around the exterior of a left ventricle 116 to the posterior side of the left ventricle 116 of a heart 108. The positioning tube 704 may be comprised of an elongate portion 708 and a curved portion 712 that may be connected together (or connectable together). For example, elongate portion 708 and a curved portion 712 may be connected or be connectable by way of a proximal bend 716. In one embodiment, the positioning tube 704 may be comprised of a single-piece, integral component that may be suitably manipulated/shaped/molded/etc. to form the curved portion 704 and the proximal bend 716. In one embodiment, the positioning tube 704 may be comprised of several separate tube segments that may be individually molded, manipulated, or fabricated and then adhered, bonded, glued, or otherwise assembled to form the shape of the positioning tube 704 illustrated in FIGS. 12A-12B.

The curved portion 712 may comprise a radius of curvature suitable for extending around the left side of the human heart 108 or for extending around another organ or portion of a body. An elbow portion 720 and a guide portion 724 may be included at a distal end/region of the positioning tube 704. The elbow 720 may be disposed at a distal end of the curved portion 712. The guide portion 724 may be disposed at a distal end of the elbow 720 or an end opposite the curved portion 712. The elbow 720 and/or the guide 724 may be adhered, bonded, glued, or otherwise affixed to the distal end of the curved portion 712. Though, in one embodiment, an elbow portion the same as or similar to elbow 720 and/or a guide portion the same as or similar to guide portion 724 could be made/formed integral with other portions as part of a single-piece positioning tube or device/catheter. In one embodiment, the elbow 720 imparts a 90-degree bend to the distal end of the curved portion 712, such that the guide 724 is oriented toward, and aligned with, a longitudinal axis 728 of the elongate portion 708, as shown for example in FIG. 12B.

Guide portion 724 may be formed in a variety of sizes and shapes. In one embodiment, the guide portion 714 may be columnar or generally columnar in shape. A front region of guide 724 (e.g., opposite the elbow 720 and/or facing toward the elongate portion 708) may be pressed or pulled against a portion of an organ or part of the body (e.g., a heart) and may cause a bending or bulging in the wall that may be visible with an echo probe or ultrasound probe or other imaging equipment. Doing this may help a user to identify and mark a desired puncture or treatment location on the organ or part of the body (e.g., on a wall of a heart). Guide portion 724 may include a concave or inwardly tapered front region (e.g., on the end opposite elbow portion 720). This front region may be curved into a concave or generally concave region or may be tapered inwardly to form a conical or generally conical region within the front end of the guide 724. This concave or inwardly tapered front region may help receive a puncturing device through the organ or part of the body, e.g., the concave or inwardly tapered front region may help guide and receive a needle or other puncture device passing through a wall of the heart. If the device/catheter 700 has only a single lumen (though some embodiments may have more) and no finger 706, applicator 732, or device connecting these are used (i.e., if these do not block the lumen of the device), then the lumen may be used to help deploy and/or use an anchor or other medical device to the puncture/treatment location. For example, a tension member of an anchor may be passed through the lumen and may be snared by the puncturing device or another device that passes through the puncture, then the puncturing device or snare may be withdrawn through the puncture bringing the tension member with it and leaving the anchor deployed outside the puncture.

The device/catheter 700 may also include a finger 706, which may be coupled with guide portion 724 and/or may reside partially or fully within guide portion 724. Finger 706 may be configured in a variety of shapes and sizes, e.g., columnar, conical, rounded, flat, curved, and many more. Finger 706 may be thick or thin and may be solid or hollow. In one embodiment, the finger 706 may be oriented toward, and aligned with, a longitudinal axis 728 of the elongate portion 708, as shown in FIG. 12B. The alignment of the finger 706 with the longitudinal axis 728 of the elongate portion 708 may help enable the surgeon to use/manipulate the proximal handle 702 such that the device/catheter 700 may be used to determine a location and orientation of the guide 724 and/or finger 706 (e.g., when located near an organ or, for example, near the posterior side of the human heart 108).

A front region of finger 706 (e.g., facing away from the elbow 720 and/or facing toward the elongate portion 708) may be pressed or moved against a portion of an organ or part of the body (e.g., a heart) to identify and mark the desired puncture or treatment location on the organ or part of the body (e.g., on a wall of a heart). The finger 706 may be slidably coupled with the guide 724. The finger 706 may be configured and designed to be movable and/or may be configured and designed to be transitionable between two or more configurations. Transitioning between the configurations or moving the finger may help the user to identify the location of the finger 706 when viewing the organ or portion of the body (e.g., heart) with an echo probe or ultrasound probe (e.g., a probe described elsewhere herein) or other imaging equipment, e.g., movement or transitioning of the finger may cause portions of an organ or heart to bend, bulge, or move in a way that can be seen with imaging equipment. If used to identify a desired puncture location on a heart, pressing the finger 706 into and/or moving the finger 706 along the side or wall of the heart may cause a slight bend or bulge in the wall of the heart that may be detectable/viewable by way of an epicardial echo probe or ultrasound probe or other imaging equipment. The finger 706 may thereby aid a surgeon in identifying a location on the wall that is suitable for being punctured (e.g., during FMR treatment) without causing damage to vessels, papillary muscles, and/or tissue structures within the left ventricle 116.

Finger 706 may be configured to retract entirely within the guide 724 or to have a portion of the finger 706 that remains outside the guide 724. In one embodiment, finger 706 may be a wire, a wire-like device, or may be another long, narrow device that can extend from the guide 724 or retract within the guide 724. In one embodiment, finger 706 may be columnar or generally columnar and may act similar to a column or button that pushes out from the guide 724 to contact and press against an organ or part of the body. In one embodiment the finger 706 may have a diameter similar to or slightly less than the guide 724. The finger 706 may slide within the guide 724 to extend out from or retract within the guide 724 and thereby transition between an extended configuration and a retracted configuration. In one embodiment, the finger 706 may include a portion with a larger diameter or width that remains outside the guide 724 (e.g., between the guide 724 and elongate portion 708) and a portion with a smaller diameter or width that slides within and partially outside the guide 724 to transition the finger 706 between an extended configuration and retracted configuration. A larger diameter region of a finger 706 may be conical or generally conical in shape (e.g., may have a region with a continuous transition from a larger diameter to a smaller diameter).

Finger 706 and/or guide724 may include a concave or inwardly tapered front region (e.g., on the end facing away from elbow portion 720 and toward elongate portion 708). This front region may be curved into a concave or generally concave region or may be tapered inwardly to form a conical or generally conical region within the front end of the finger 706 or guide 724. This concave or inwardly tapered front region may help receive a puncturing device through the organ or part of the body, e.g., the concave or inwardly tapered front region may help guide and receive a needle or other puncture device passing through a wall of the heart.

The finger 706 may be moved and/or transitioned between configurations (e.g., extended and retracted) by way of a long, flexible catheter shaft, wire, tube, pusher, etc. that extends from the finger 706 to an applicator 732, which applicator 732 may be disposed near the proximal end of the catheter/device 700 or near handle 702. The catheter shaft, wire, tube, pusher, etc. may be routed from the finger 706, within a lumen of the curved portion 712, and to the applicator 732. An actuator tube 736 may act as the flexible catheter shaft, wire, tube, pusher, etc. that extends through the curved portion 712 to the finger 706 to cause the finger 706 to move or transition between configurations, or the actuator tube 736 maybe provide a connecting lumen through which the flexible catheter shaft, wire, tube, pusher, etc. passes from the applicator 732 to the curved portion 712. The actuator tube 736 may be slidable within or otherwise connected, adhered, bonded, glued, or affixed to the curved portion 712 to ensure that the finger 706 moves as directed by movement of the applicator 732 (e.g., a user should be able to move the applicator 732 to cause the finger to move or transition between configurations).

The device/catheter 700 may further include a spring, or other biasing component, that biases the finger 706 to a retracted configuration (e.g., biases the finger 706 toward or within the guide 724 and/or elbow 720). In one embodiment, the spring may be coupled between the applicator 732 and the actuator tube 736 and/or within the applicator 732, such that when a pressing force is applied to the applicator 732, the spring is compressed and the flexible catheter shaft, wire, tube, pusher, etc. moves distally and pushes the finger 706 to an extended configuration (e.g., such that the finger 706 can push against a wall of a heart, organ, or other part of the body). In one embodiment, the spring may bias the applicator 732 or a portion of the applicator 732 proximally away from the actuator tube 736, such that after the pressing force is no longer applied to the applicator 732 the spring automatically moves the flexible catheter shaft proximally and pulls the finger 706 toward and/or within the guide 724. It should be understood that the spring, or other biasing component, is not to be limited to being disposed between the applicator 732 and the actuator tube 736, but rather the spring, or other biasing component may be disposed in any location of the puncture location catheter 700 that is suitable for biasing the finger 706 toward the guide 724, as described herein. For example, in one embodiment, the spring or biasing component may be disposed within the guide 724.

In one embodiment, e.g., as shown in FIGS. 12A-12C, the long, thin positioning tube 704 may comprise at least one interior lumen that is dedicated to routing the flexible catheter shaft, wire, tube, pusher, etc. from the applicator 732 to the finger 706, as described above. In one embodiment, the positioning tube 704 may comprise more than one interior lumen, e.g., two, three, or four interior lumens, without limitation. In one exemplary embodiment, the positioning tube 704 may comprise at least (1) a first lumen that may be used to direct the flexible catheter shaft, wire, tube, pusher, etc. to the finger 706, as described herein, and (2) a second lumen that may be used to help deploy an anchor (e.g., the superior anchor 136, 137) or other medical device during medical treatment. For example, during FMR treatment, the finger 706 through the first lumen may be used to help guide a needle catheter (e.g., a 4 or 5 French-sized needle catheter) or other puncturing device to puncture wall of the heart 108 (e.g., to puncture a wall of the left ventricle 116) in a desired puncture location, and the second lumen may be used to deploy a tension member (e.g., tension member128) and an anchor (e.g., superior anchor 136, 137) to the puncture site. For example, a tension member of an anchor may be passed through the second lumen and may be snared by the puncturing device or another device that passes through the puncture, then the puncturing device or snare may be withdrawn through the puncture bringing the tension member with it and leaving the anchor deployed outside the puncture. Similarly, if two lumens are not included within device/catheter 700, multiple separate single lumen devices could be used in a similar way, e.g., the lumen of the first device may help control a finger 706, and the lumen of a second device may aid in deployment and/or use of an anchor or other medical device.

In one embodiment, upon withdrawing the puncturing device/needle from the catheter, a snare may be inserted into the catheter and directed through the puncture in the organ (e.g., the puncture in a wall of the heart 108) to capture an end of the tension member 128 extended or pushed out of a lumen (e.g., a second lumen of device/catheter 700). The snare may then be used to draw the tension member 128 through the wall of the organ/heart and to pull the superior anchor 136 from the second lumen into contact with the exterior of the posterior wall of the heart 108. The tension member 128 extend across the left ventricle 116, through the wall of the septum 132 to an inferior anchor deployed at the septum, or through the wall of the septum 132 and across the right ventricle 120 to an inferior anchor outside the right ventricle. The inferior anchor may be mounted onto and/or connected to the end of the tension member 128 and may be positioned adjacent to the right ventricle 120 (e.g., external to the heart outside the right ventricle as shown in FIGS. 1-2) or may be positioned inside the right ventricle against the wall of the septum 132. The inferior anchor 140, 141 may be cinched or otherwise locked/attached onto the tension member 128 to impart an advantageous shape change to the heart and/or annulus of the mitral valve 112, as well as to advantageously reposition the papillary muscles 144, as described herein.

Anchoring systems and systems for setting an anchor described herein may include any of the instruments and components described above (e.g., the needles, catheters, introducer systems/assemblies, trocars, trocar catheters, ultrasound probe systems, anchors, etc. described herein). The systems may be configured or used for a wide variety of cardiac treatments or procedures, such as, by way of non-limiting example, treatment of functional mitral valve incompetencies (e.g., mitral valve regurgitation), treatment of functional atrial valve incompetencies, and the like. The systems may include a delivery catheter having a lumen; a self-expandable anchor for fixating a mitral valve splint, the anchor having a low profile configuration in which it may be positioned inside the lumen of the delivery catheter and a deployed, expanded configuration configured to anchor the mitral valve splint, wherein the self-expandable anchor is configured to transition automatically to the deployed, expanded configuration when it exits the delivery catheter. The self-expandable anchor may be the same as or similar to anchor 148 described herein. The systems may also include an ultrasound probe system including an ultrasound probe and a guide, the guide may be configured for or be capable of guiding the delivery catheter to a desired location in the body or heart. The ultrasound probe may include an ultrasound transducer. The ultrasound probe may be configured to allow a user to view the various medical instruments or other components of the system and internal tissue of the body during treatment. For example, the ultrasound probe may include an ultrasound transducer and may be configured to allow a user to view the self-expandable anchor and tissue of the heart during deployment of the anchor inside a patient.

A method for treatment of the human heart (e.g., for treating mitral valve issues) may include various steps described herein. For example, the method may include loading a medical instrument into a guide attached to an ultrasound probe. The method may also comprise attaching the guide to the ultrasound probe. This can be done in several different ways, including by way of a proximal coupling and a distal coupling such that the guide is parallel to the elongate shaft and a distal end of the medical instrument is adjacent to the distal end of the ultrasound probe. The ultrasound probe may include any of the features described with respect to ultrasound probes and ultrasound probe systems herein. The ultrasound probe may be a trans-vaginal ultrasound probe or a specially configured ultrasound probe (e.g., an ultrasound probe configured for treatment of mitral valve issues). The ultrasound probe may comprise an elongate shaft extending from a proximal handle to a distal end. The ultrasound probe may include an ultrasound transducer, e.g., in the distal end of the ultrasound probe.

The method may also include inserting the ultrasound probe into a patient by way of an opening in skin of the patient (e.g., an incision in the skin). Inserting the ultrasound probe may comprise advancing the distal end of the ultrasound probe and the distal end of the medical instrument together within the patient. The method may also include navigating the distal end of the ultrasound probe to a desired location in the body (e.g., to a location adjacent to an exterior surface of the heart or pericardium). Identifying a treatment site may comprise identifying a puncture site on the exterior surface. Navigating the distal end of the ultrasound probe to the location may comprise viewing tissues and structures within the patient by way of the ultrasound transducer, such that injury to the tissues and structures due to advancing the distal end of the ultrasound probe and the distal end of the transcatheter are minimized. The ultrasound transducer may be configured to provide a relatively wide view of tissues and structures directly in front of the distal end of the ultrasound probe during navigating the distal end of the ultrasound probe to the location.

The method may include identifying a treatment site (e.g., on the exterior surface) using the ultrasound probe to view the internal tissues, structures, etc. of the body. For example, identifying a treatment site may include viewing an image (e.g., a live or real-time image) or images obtained using an ultrasound transducer of the ultrasound probe, the ultrasound transducer may be disposed within the distal end of the ultrasound probe. The method may also include advancing the medical instrument within the guide to the treatment site; and using the medical instrument at the treatment site. Using the medical instrument at the treatment site may include puncturing or cutting tissue at the treatment site, deploying a medical instrument or portion of a medical instrument, merely passing the medical instrument through tissue at the treatment site to move the medical instrument to a second treatment site, a third treatment site, and/or additional treatment site(s), and/or other uses. The method may also include withdrawing the medical instrument away from the treatment site and/or heart. The medical instrument may be any of the medical instruments described herein. For example, the medical instrument may comprise a trocar catheter (e.g., the same as or similar to trocar catheter 200 described herein), and using the medical instrument at the treatment site may comprise using an actuator to deploy a trocar distal tip of the trocar catheter to puncture the exterior surface at a puncture site.

The medical instrument may also comprise a flexible needle (e.g., the same as or similar to the flexible needle 432 described herein), and identifying a treatment site may comprise identifying a first puncture site on the exterior surface, e.g., based on observing structures on the exterior surface and within the heart using the ultrasound transducer. Using the medical instrument at the treatment site may also comprise using the flexible needle to puncture the exterior surface at the first puncture site. The method may further comprising identifying a second treatment site or puncture site on a septal wall of the heart (e.g., of the septum between right and left ventricles) using the ultrasound transducer, and using the medical instrument at the treatment site may comprise passing the flexible needle through the septal wall into the left ventricle of the heart at the second puncture site. The method may further comprise identifying a third puncture site on a posterior wall of the left ventricle of the heart using the ultrasound transducer, and using the medical instrument at the treatment site may further comprise puncturing the posterior wall at the third puncture site. Puncturing the posterior wall may comprise using the flexible needle or may comprise extending an inner curved needle from the flexible needle through the posterior wall at the third puncture site.

Identifying the third puncture site on a posterior wall of the left ventricle using the ultrasound transducer may also include using puncture location device/catheter (e.g., similar to catheter/device 700). Any of the steps described above for use of a puncture location device/catheter may be used. A device/catheter (e.g., C-shaped device/catheter or a puncture-location device/catheter, which may be the same as or similar to other such devices/catheter described elsewhere herein and/or shown in FIGS. 12A-12C), may optionally be used to identify the third puncture site or another desired puncture site/locations. The device/catheter may be inserted through an incision on the chest of a patient and navigated around a portion of the heart (e.g., to a posterior wall of the left ventricle). Identification of the puncture site may be done by moving, pressing, pulling, etc. a portion of the device/catheter against a wall (e.g., an external wall) of the heart while viewing the wall of the heart with imaging equipment (e.g., an echo or ultrasound probe). The moving, pressing, pulling, etc. of the device/catheter may be done so as to cause the wall of the heart to bend or bulge in a manner that is visible on the imaging equipment. The catheter/device may include a movable finger to aid in moving or pressing against the wall of the heart. The method may involve transitioning the finger from a retracted configuration to an expanded configuration to press against the wall. The method may include moving the device/catheter and/or finger along the wall until a desired puncture location/site (e.g., the third puncture site) is reached. The method may include viewing the wall with imaging equipment (e.g., the ultrasound probe or a probe/equipment described elsewhere herein) and identifying a desired puncture location (e.g., the third puncture site) when the device/catheter and/or finger cause the desired puncture location to bend or bulge. The method may include identifying the desired puncture location (e.g., the third puncture site) as a location on the wall away from blood vessels and/or papillary muscles, e.g., when the bend/bulge appears on the wall in a location away from the blood vessels and/or papillary muscles.

The method may also include creating an incision or hole (e.g., puncturing and/or positioning a needle or introducer) in the left and/or posterior wall of the left ventricle from inside the left ventricle to outside the left ventricle. If the device/catheter above is used to identify the desired puncture location (e.g., the third puncture site), puncturing the wall may include directing a puncturing instrument and/or introducer at the desired puncture location and/or at a bulge/bend in the wall caused by the device/catheter above. The device/catheter may include a concave or inwardly tapered surface that can help guide and receive the puncturing instrument.

The method may further comprise treating a condition of the heart by fixating a splint within the heart using at least one anchor (e.g., a superior anchor and/or an inferior anchor) so as to alter a geometric shape of the heart. The condition of the heart to be treated may be mitral valve incompetency and the splint may be a mitral valve splint. Treating the condition of the heart may further comprise treating the mitral valve incompetency by fixating the mitral valve splint within the heart using at least one anchor (e.g., a superior and inferior anchor as shown in FIGS. 1-2). The at least one anchor may comprise an anchor suitable for deployment from a lumen of a delivery catheter, wherein the self-expandable anchor is configured to contact an exterior surface of the heart or pericardium adjacent a left ventricle. Optionally, using the medical instrument at the treatment site may comprise deploying an anchor through a flexible curved needle (e.g., similar to the flexible needles described elsewhere herein). The method may also include placing the anchor in contact with an exterior surface of the heart or pericardium adjacent the left ventricle of the heart. The anchor may be the same as or similar to anchor 148 described herein.

In some embodiments, the method may comprise other medical treatments, for example, treating a condition of the heart by replacing at least one native valve within the heart using a prosthetic valve (e.g., a prosthetic mitral valve and/or a prosthetic aortic valve). The condition of the heart to be treated may be mitral valve incompetency and/or aortic valve incompetency. Delivery of the prosthetic mitral valve or the prosthetic aortic valve may be accomplished in various ways. For example, the prosthetic valve may be delivered by way of a transapical approach whereby access to the left ventricle is achieved through an incision in the chest and an incision in the apex of the heart. Alternatively, the prosthetic valve may be delivered by way of a transatrial approach through the left atrium. For example, the transatrial approach may be performed by way of an incision in the chest and an incision through the atrial wall of the heart. In any case, when an incision is made, the systems/assemblies described herein may be used to guide the incisions and/or to guide medical instruments (e.g., needle, catheter, cutting instrument, and/or delivery device) more accurately to a target location.

In one embodiment, a method for treatment of the human heart may comprise one or more of the following steps: loading a medical instrument into a guide attached to a trans-vaginal ultrasound probe, the trans-vaginal ultrasound probe comprising an elongate shaft extending from a proximal handle to a distal end; inserting the trans-vaginal ultrasound probe into a patient by way of an opening in skin of the patient; navigating the distal end of the trans-vaginal ultrasound probe to a location adjacent to an exterior surface of the heart or pericardium; identifying a first treatment site on the exterior surface based on data about the exterior surface obtained using an ultrasound transducer disposed within the distal end of the trans-vaginal ultrasound probe; advancing the medical instrument within the guide to the first treatment site; using the medical instrument at the first treatment site; identifying a second treatment site on an interior wall of the heart based on data about the interior wall obtained using the ultrasound transducer; advancing the medical instrument within the guide to the second treatment site; using the medical instrument at the second treatment site; and withdrawing the medical instrument from the heart.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims. Further, features and/or steps described with respect to particular systems, apparatuses, methods, etc. herein may be used with other systems, apparatuses, methods, etc. described herein even if not expressly described with respect to those systems, apparatuses, methods, etc. Further, while treatments described may be focused on the heart, the systems, apparatuses, methods, etc. may be used in other treatments.

What is claimed is:

1. A method for treatment of a heart, the method comprising:
 loading a flexible needle into a guide attached to an ultrasound probe, the ultrasound probe comprising an elongate shaft extending from a proximal handle to a distal end of the ultrasound probe;
 inserting the ultrasound probe into a patient by way of an opening in skin of the patient;
 navigating the distal end of the ultrasound probe to a location adjacent to an exterior surface of the heart or pericardium;
 identifying a first puncture site on the exterior surface based on observing structures on the exterior surface and within the heart using an ultrasound transducer disposed within the distal end of the ultrasound probe;
 advancing the flexible needle to the first puncture site using the guide;
 using the flexible needle to puncture the exterior surface at the first puncture site;
 identifying a second puncture site on a septal wall of the heart using the ultrasound transducer;
 passing the flexible needle through the septal wall into a left ventricle of the heart at the second puncture site;
 identifying a third puncture site on a posterior wall of the left ventricle of the heart using the ultrasound transducer;
 using the flexible needle to puncture the posterior wall at the third puncture site; and
 withdrawing the flexible needle away from the third puncture site.

2. The method of claim 1, further comprising attaching the guide to the ultrasound probe by way of a proximal coupling and a distal coupling such that the guide is angled at a fixed angle with respect to the elongate shaft and a distal end of the flexible needle is adjacent to the distal end of the ultrasound probe.

3. The method of claim 1, wherein inserting the ultrasound probe comprises advancing the distal end of the ultrasound probe and the distal end of the flexible needle together within the patient.

4. The method of claim 1, wherein navigating the distal end of the ultrasound probe to the location comprises viewing tissues and structures within the patient by way of the ultrasound transducer, such that injury to the tissues and structures due to advancing the distal end of the ultrasound probe and the flexible needle are minimized.

5. The method of claim 4, wherein the ultrasound transducer is configured to provide a view of tissues and structures directly in front of the distal end of the ultrasound probe during navigating the distal end of the ultrasound probe to the location.

6. The method of claim 1, further comprising treating a condition of the heart by fixating a splint within the heart using at least one anchor so as to alter a geometric shape of the heart.

7. The method of claim 6, wherein the condition of the heart is mitral valve incompetency and the splint is a mitral valve splint, and wherein treating the condition of the heart further comprises treating the mitral valve incompetency by fixating the mitral valve splint within the heart using the at least one anchor.

8. The method of claim 6, wherein the at least one anchor comprises a self-expandable anchor suitable for deployment from a lumen of a delivery catheter, wherein the self-expandable anchor is configured to contact an exterior surface of the heart or pericardium adjacent the left ventricle of the heart.

9. The method of claim 6, wherein the at least one anchor is configured to move from a low profile configuration to an expanded configuration, and includes a cover peripherally supported by a ring when the at least one anchor is in the expanded configuration.

10. The method of claim 1, wherein the flexible needle includes a plurality of slits along a length thereof, and wherein puncturing the posterior wall comprises extending an inner curved needle from the flexible needle through the posterior wall at the third puncture site.

11. The method of claim 1, further comprising deploying an anchor through the flexible needle and placing the anchor in contact with an exterior surface of the heart or pericardium adjacent the left ventricle of the heart.

12. The method of claim 1, wherein the ultrasound probe is a trans-vaginal ultrasound probe, and wherein inserting the ultrasound probe into the patient comprises inserting the trans-vaginal ultrasound probe into the patient.

13. A method for treatment of the human heart, the method comprising:
 loading a flexible needle into a guide attached to a trans-vaginal ultrasound probe, the trans-vaginal ultrasound probe comprising an elongate shaft extending from a proximal handle to a distal end;
 inserting the trans-vaginal ultrasound probe into a patient by way of an opening in skin of the patient;
 navigating the distal end of the trans-vaginal ultrasound probe to a location adjacent to an exterior surface of the heart or pericardium;
 identifying a first puncture site on the exterior surface based on observing structures on the exterior surface and within the heart using an ultrasound transducer disposed within the distal end of the trans-vaginal ultrasound probe;
 advancing the flexible needle to the first puncture site using the guide;
 using the flexible needle to puncture the exterior surface at the first puncture site;
 identifying a second puncture site on an interior wall of the heart based on data about the interior wall obtained using the ultrasound transducer;
 advancing the flexible needle to the second puncture site;
 passing the flexible needle through a wall of a septum of the heart and into a left ventricle of the heart at the second puncture site;

identifying a third puncture site on a posterior wall of the left ventricle of the heart using the ultrasound transducer;

using the flexible needle to puncture the posterior wall at the third puncture site; and withdrawing the flexible needle from the third puncture site.

14. The method of claim 13, further comprising treating a condition of the heart by fixating a splint within the heart using at least one anchor so as to alter a geometric shape of the heart.

15. The method of claim 14, wherein the at least one anchor is configured to move from a low profile configuration to an expanded configuration, and includes a cover peripherally supported by a ring when the at least one anchor is in the expanded configuration.

16. The method of claim 14, wherein the condition of the heart is mitral valve incompetency and the splint is a mitral valve splint, and wherein treating the condition of the heart further comprises treating the mitral valve incompetency by fixating the mitral valve splint within the heart using the at least one anchor.

17. The method of claim 14, wherein the at least one anchor comprises a self-expandable anchor suitable for deployment from a lumen of a delivery catheter, wherein the self-expandable anchor is configured to contact an exterior surface of the heart or pericardium adjacent the left ventricle of the heart.

18. The method of claim 13, further comprising deploying an anchor through the flexible needle and placing the anchor in contact with an exterior surface of the heart or pericardium adjacent the left ventricle of the heart.

19. An anchoring system for treatment of functional mitral valve regurgitation, comprising:

a delivery catheter including a lumen;

a self-expandable anchor for fixating a mitral valve splint, the self-expandable anchor having a low profile configuration in which the self-expandable anchor may be positioned inside the lumen of the delivery catheter and having an expanded configuration configured to anchor the mitral valve splint, wherein the self-expandable anchor is configured to transition to the expanded configuration outside the delivery catheter, wherein the self-expandable anchor comprises a wire having atraumatic ends which meet at a break, the wire capable of being straightened from a ring-shaped configuration in the expanded configuration to a straightened configuration to transition the self-expandable anchor into the low profile configuration, the self-expandable anchor also comprising a cover supported by the wire, and wherein the cover is engaged with a cord such that pulling the cord tightens the cover into a cone-like configuration; and an ultrasound probe system including an ultrasound probe and a guide, the guide capable of guiding the delivery catheter to a desired location, wherein the ultrasound probe is configured to allow a user to view the self-expandable anchor and tissue of the heart during deployment of the self-expandable anchor inside a patient.

20. The anchoring system of claim 19, wherein the cover is peripherally supported by the wire and includes a central portion that engages the cord when the self-expandable anchor is in the expanded configuration.

* * * * *